United States Patent [19]

Welch et al.

[11] Patent Number: 5,712,481
[45] Date of Patent: *Jan. 27, 1998

[54] PROCESS AND APPARATUS FOR ANALYSIS OF HYDROCARBON SPECIES BY NEAR INFRARED SPECTROSCOPY

[75] Inventors: William T. Welch, Ashland, Ky.; Michael B. Sumner, Huntington, W. Va.; Brian K. Wilt, Ashland, Ky.; Roy Roger Bledsoe, Huntington, W. Va.; Steven M. Maggard, Ashland, Ky.

[73] Assignee: Ashland Inc, Ashland, Ky.

[ * ] Notice: The term of this patent shall not extend beyond the expiration date of Pat. No. 5,349,188.

[21] Appl. No.: 685,364

[22] Filed: Jul. 23, 1996

Related U.S. Application Data

[63] Continuation of Ser. No. 305,233, Sep. 13, 1994, abandoned, which is a continuation-in-part of Ser. No. 506,391, Apr. 9, 1990, Pat. No. 5,349,188.

[51] Int. Cl.$^6$ .................................................. G01J 5/02
[52] U.S. Cl. ............................ 250/339.12; 250/343
[58] Field of Search .............................. 250/343, 339.12

[56] References Cited

U.S. PATENT DOCUMENTS

| | | | |
|---|---|---|---|
| 4,963,745 | 10/1990 | Maggard | 250/343 |
| 5,046,846 | 9/1991 | Ray et al. | 250/339.12 |
| 5,145,785 | 9/1992 | Maggard et al. | 436/8 |
| 5,223,714 | 6/1993 | Maggard | 250/343 |
| 5,243,546 | 9/1993 | Maggard | 364/571.02 |
| 5,349,188 | 9/1994 | Maggard | 250/339 |
| 5,349,189 | 9/1994 | Maggard | 250/339.12 |

FOREIGN PATENT DOCUMENTS

| | | | |
|---|---|---|---|
| 9115762 | 10/1991 | WIPO | G01N 33/28 |
| 9324823 | 12/1993 | WIPO | G01N 21/35 |

OTHER PUBLICATIONS

"Quantative aspects of near-infrared Fourier transform Raman spectroscopy" by F.T. Walder and M.J. Smith; Nicolet Instrum. Corp., Madison, WI; Spectrochim Acta, Part A (1991), v. 47A(9–10) pp. 1201–1216.

"Quantative Analyse von Benzol–Toluol–Paraffin–Mischungen im Nahen Infrarot" by Hans Jurgen Leimer and Jurgen Schmidt; VEB Petrochem Komb; Chem. Tech. (Lupzig)(1973), 25(2), 99–100.

"Carbon Number Prediction from Herschel–Infrared Spectra Using Partial Least–Squares Regression" by Garin D. Schrieve and Alan H. Ullman; The Procter & Gamble Co., Cincinnati, OH; Appl. Spectrosc. (1991), 45(4), 713–14.

"Predicting Gasoline Properties Using Near–IR Spectroscopy Beyond Octane Numbers and Hydrocarbon Classes"by Stephen J. Swarin and Charlene A. Drumm; Anal. Chem. Dep., Gen. Motors, Warren, MI; Spectroscopy (1992) 7(7) 42–49.

(List continued on next page.)

*Primary Examiner*—Don Wong
*Attorney, Agent, or Firm*—Richard C. Willson, Jr.; Richard D. Stone

[57] ABSTRACT

In addition to analysis in the infrared spectra of hydrocarbon group types, it has now been found that certain hydrocarbon species, including preferably aromatic species such as benzene, toluene, xylene, and alkyl benzenes such as ethyl benzene, can be determined by measuring absorption in certain selected wavelengths in the infrared spectra, then manipulating the data, e.g., preferably by taking the first or higher derivative, and applying statistical techniques, preferably multiple linear regression (MLR) to provide an output signal indicative of the concentration of the particular specie. The output signal can be used to control refinery and chemical processes, e.g., reforming, catalytic cracking, alkylation and isomerization. In manufacturing reformulated fuels, government regulations can be complied with by utilizing the invention to blend fuels which have a maximum of benzene or other regulated components.

18 Claims, 8 Drawing Sheets

OTHER PUBLICATIONS

"Precision of the Petrochemical Process Analysis using NIR Spectroscopy" by Davidson, DeConde, Hake, Tracy, Gantz and McDermott; Perkin–Elmer Corp., Panama, CA; Proc. SPIE—Int. Soc. Opt. Eng. (1992) 231–235.

"Using Short–Wave Near Infrared Spectroscopy for the Analysis of Petrochemicals" by Davidson, DeConde, Hake, Tracy, Gantz and McDermott; Perkin–Elmer Corp., Pomona, CA; Adv. Instrum. Control (1992) pp. 83–91.

"A Fluid–Portable, Fiber–Optics Based Near–Infrared Spectrometer and its Applications to Fuels" by M.J. Lysaght; Air Force Inst. Tech., Wright–Patterson AFB, OH; Report (1991) AFIT/CI/CIA–91–013d; Order#AD–A239310, 258 pp.; Avail: NTIS; from Gov. Announce. Index (U.S.) 1991, 91(23), Abstr #164,244.

"Better Alkylation Control" by Ryskamp, McGee, and Badavas, Hydrocarbon Processing (1986); vol. 65(11); pp. 113–118.

"Better Alky Control Pays" by Funk and Feldman Applied Automation Inc., Bartlesville, OK; Hydrocarbon Processing (1983), pp. 92–95; vol. 62 (11).

"On–line Octane Control with NIR Analyzers" by M.S. Zetter and B.A. Politzer; Hydrocarbon Processing (1983) Mar.; pp. 103–106.

CONTINUOUS CATALYST REGENERATION (CCR) CATALYTIC REFORMER

FIG. 3 DISPLAY OF 52 SECOND DERIVATIVE SPECTRA ACROSS ENTIRE RANGE

A SCHEMATIC DRAWING OF A MULTI-STREAMING FEED FORWARD NEAR INFRARED BLENDING ANALYZER SYSTEM WITH FEED BACK CAPABILITY

FIG. 5 ISOMERIZATION UNIT WITH PENTANE RECYCLE

UOP ETHERMAX PROCESS

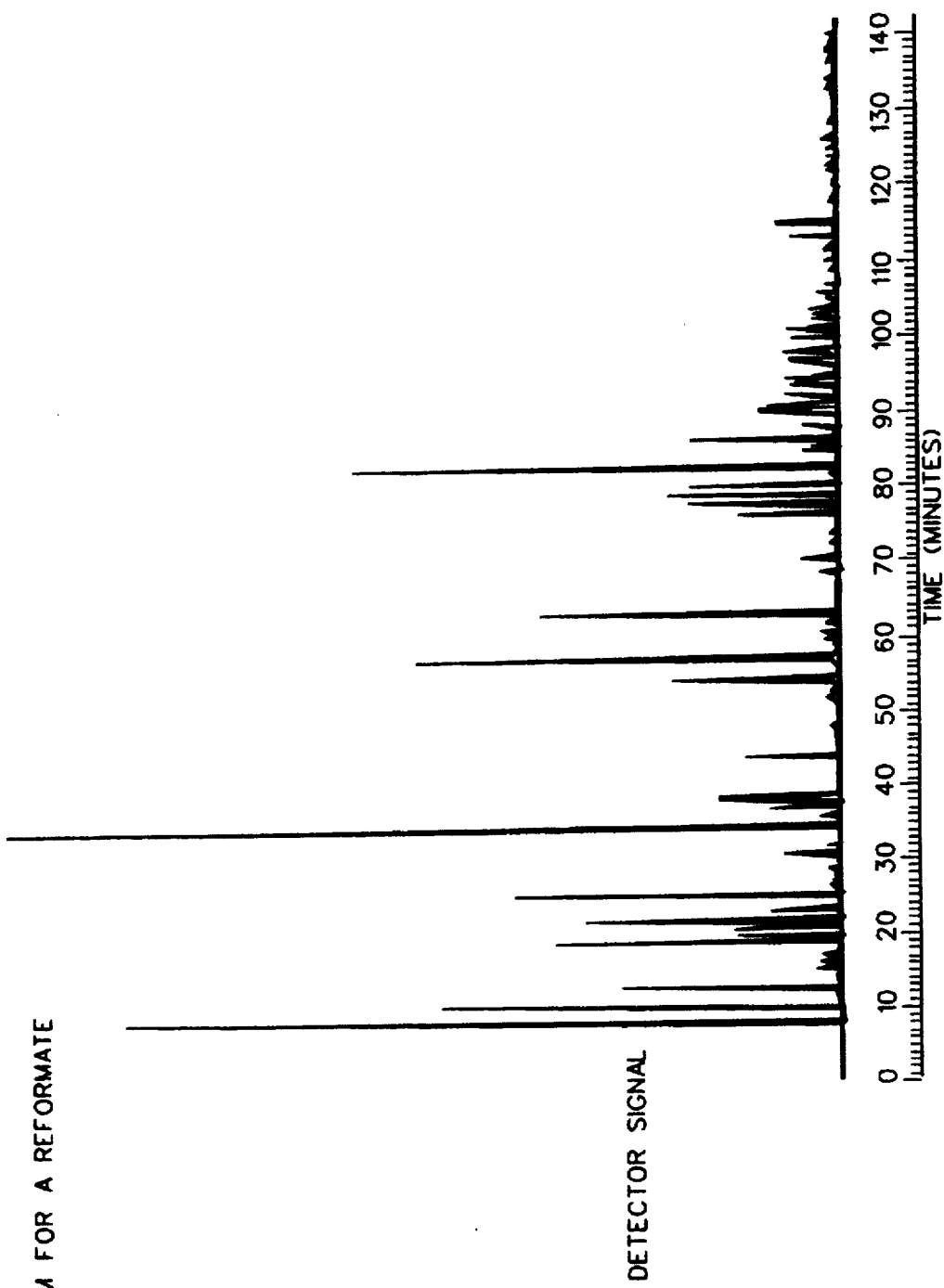
FIG. 8 PIANO CHROMATOGRAM FOR A REFORMATE

PROCESS AND APPARATUS FOR ANALYSIS OF HYDROCARBON SPECIES BY NEAR INFRARED SPECTROSCOPY

CROSS REFERENCE TO RELATED APPLICATIONS

This application is a continuation of application Ser. No. 08/305,233, filed 13 Sep. 1994, now abandoned, which is a continuation-in-part of Ser. No. 07/506,391 filed Apr. 9, 1990 now U.S. Pat. No. 5,349,188, issued Sep. 20, 1994, (attorney docket 6362AUS).

U.S. Pat. No. 5,349, 188, issued Sep. 20, 1994 (attorney docket 6362AUS) and U.S. Pat. No. 5,349,189, issued Sep. 20, 1994, (attorney docket 6362BUS) relate to the general field of the present invention.

U.S. Pat. No. 5,349,188, issued Sep. 20, 1994, (attorney docket 6362AUS) teaches the determination of octane generally, and U.S. Pat. No. 5,349,189, issued Sep. 20, 1994, (attorney docket 6362BUS) teach the determination of hydrocarbon groups by group type analysis, e.g., "PIANO" or "PIONA." PIANO (see procedure taught by Analytical Automation Specialists, Inc., "The Detailed Analysis of Petroleum Naphthas, Reformates, Gasoline and Condensates by High-Resolution Gas Chromatography", operators manual, P.O. Box 80653, Baton Rouge, La. 70898) and PIONA (see e.g., Eberly, Paul E., U.S. Pat. No. 5,322,619) are both gas chromatographic methods which differ in the selection of absorbent columns for the separation.

BACKGROUND OF INVENTION

I. Field of the Invention

The present invention relates to techniques of analysis, particularly of hydrocarbon and substituted hydrocarbon mixtures, generally classified in U.S. Class 250.

II. Description of the Prior Art

Prior patents in this field include U.S. Pat. No. 4,963,745 to Maggard issued Oct. 16, 1990 (attorney docket 6353AUS); U.S. Pat. No. 5,223,714 to Maggard issued Jun. 29, 1993 (attorney docket 6360AUS); U.S. Pat. No. 5,243, 546 to Maggard issued Sep. 7, 1993 (attorney docket 6379AUS); U.S. Pat. No. 5,145,785 to Maggard and Welch issued Sep. 8, 1992 (attorney docket 6384AUS); international application WO 93/24823 published Dec. 9, 1993 (attorney docket 6411APC).

U.S. Pat. No. 5,349,188 to Maggard, issued Sep. 20, 1994, (attorney docket 6362AUS) teaches the determination of octane generally, and U.S. Pat. No. 5,349,189 to Maggard, issued Sep. 20, 1994, (attorney docket 6362BUS) teaches the determination of hydrocarbon groups by group type analysis, e.g., "PIANO".

Prior art teachings of the determination of individual hydrocarbon group types such as paraffins, isoparaffins, aromatics, naphthenes, and olefins (PIANO) can be found in prior literature and patents. A preferred technique is gas liquid chromatography, wherein a sample is injected into an absorbent column swept by an elutriating inert gas, e.g., helium and the elapsed time for arrival at the end of the column is measured for each of the components, e.g., by a flame ionization detector, thermal conductivity, or other detector, as shown in Example 11 and FIG. 8.

Conventionally, the percents of each of the individual compounds detected by gas chromatography are grouped under their respective generic classifications in the PIANO classification system, and the relative percentage of each of the compounds (species) is determined in weight percent, volume percent, or mol percent as required. An example of this procedure is that taught by Analytical Automated Specialists, Inc., the detailed analysis of a reformate as shown in Example 11 and Table H.

These prior techniques normally require hours and neither provides the fast analysis (less than one minute) available from the present invention. The speed of analysis obtainable by the present invention enables on-line control response times not possible with past prior art chromatographic methods.

By speciation (determining the content of individual chemical compounds, e.g., benzene, xylenes, toluene), the spectral analysis of the invention can be applied to provide much of the analysis of specific species which formerly was accomplished primarily by conventional gas liquid chromatography, an inherently slow process because of the need to elutriate a sample through the chromatography column to separate it into its individual species.

The repeatability, precision and accuracy of spectral analysis would be valuable if it could be applied to speciation (e.g., to determine individually benzene, toluene, xylene, ethyl-benzene, and other desired species). This would be useful in refining the control of reformers which are conventionally controlled by merely measuring octane, or at most, octane and aromatics. By speciation, reformer control could be converted to become more sensitive to individual species. This would be valuable where a reformer is being run for petrochemical products, e.g., xylenes. It would also be valuable where reformulated fuels mandate maximum content of benzene. By analyzing for the specific species, the control can be more delicately balanced and economics further optimized.

SUMMARY OF THE INVENTION

I. General Statement of the Invention

The present invention utilizes a combination of selected NIR wavelengths together with mathematical techniques and statistical techniques in which measurements of absorption are made and combines these with multiple regression analysis, or other statistical technique and modeling to differentiate the concentration of individual hydrocarbon species. The invention is particularly preferred for the determination of the concentration of individual aromatic species such as benzene, toluene, xylene, alkyl benzenes. Particularly preferred is determination of ethyl benzene. Other hydrocarbon species in concentrations above 0.1%, more preferably above 1.0%, can be determined.

Species Concentration Measurement

The techniques of the present invention are highly useful for the determination of hydrocarbon species, preferably such as aromatic, paraffin, isoparaffin or olefin species by:
  a. measuring at at least one wavelength the near infrared absorbance in the bands of:
    1. For benzene: 2100–2160 nanometers (nm) and/or 1600–1670 nm and/or 1780–1858 nm; and/or 1120–1260 nm; and/or 850–925 nm;
    2. For toluene: 1600–1670 nm and/or 1780–1858 nm and/or 1214–1230 nm; and/or 2000–2160 nm; and/or 860–910 nm; and/or 975–1000 nm;
    3. For xylenes: 1320–1530 nm and/or 2000–2040 nm and/or 1600–1670 nm; and/or 1120–1214 nm; and/or 1780–1858 nm; and/or 2100–2160 nm; and/or 850–930 nm; and/or 940–990 nm; and/or 1015–1045 nm;
    4. For alkyl benzenes: 1156–1264 nm; and/or 1600–1670 nm; and/or 1214–1230 nm; and/or 1320–1480 nm; and/or 850–900 nm; and/or 1015–1045 nm; and/or 1214–1264 nm, and/or 1970–2040 nm; more preferably 1214–1264 nm and 1970–2040 nm;

5. For n-pentane, n-hexane n-heptane and/or other n-paraffins: 1156–1264 nm; and/or 1320–1480 nm; and/or 1600–1670 nm; and/or 1780–1858 nm; and/or 1940–2100 nm;
6. For isopentane, 2-methyl hexane, 2,2-dimethylbutane, 2,3-dimethylbutane, 2-methylpentane, 3-methylpentane and/or other isoparaffins: 1156–1264 nm; and/or 1320–1500 nm; and/or 1560–1670 nm; and/or 1780–1858 nm, and/or 1900–2160 nm;
7. For methylcyclopentane and/or other naphthenes: 1156–1430 nm; and/or 1780–1858 nm;
8. For isobutylene and/or other olefins: 1132–1214 nm; and/or 1600–1670 nm;

b. taking each of the absorbances measured, or a mathematical function thereof;

c. performing multiple regression analysis, partial least squares analysis, or other statistical treatment using the above absorbances or functions as individual independent variables, d. assigning and applying weighting constants or their equivalents to said independent variables, e. applying the above steps using known compositions to calibrate the instrument and determine said weighting constants or equivalents, f. repeating said steps with unknown compositions, applying the weighting constants or equivalents determined during said calibration with known compositions.

The hydrocarbon compositions may flow substantially intermittently or continuously past the point where the measurements are being made. The mathematical function may be a first, second, or third or higher derivative of said absorption of said band being measured, the hydrocarbon stream being measured may preferably be a reformer product stream, a catalytic cracker product stream, a gasoline blending component, or a blended gasoline product stream, and the species measured may preferably be benzene, toluene, xylenes, alkyl benzenes, most preferably ethyl benzene, and may also be h n-propyl benzene, heptane, and hexane.

As discussed briefly below and in the copending applications aforementioned, the signal may control a fuel blending system feeding blending components having different benzene contents into a common zone, whereby a fuel product having a desired benzene product is produced, or may control blending under a different species other than benzene, e.g., ethyl benzene or xylene, etc.

Signal Processing

As those skilled in the art will be aware, the absorbance signal from the measurement of the characteristic hydrocarbon species bands, used either solely or in conjunction with other bands, will preferably be mathematically processed to provide derived signals which are indicative of the concentrations (or property) being measured. Preferred techniques for mathematical processing are absorbance base line off-set corrected absorbance data; taking the first, second, third, fourth or higher derivative of the absorbance spectrum; the technique of dividing the absorbance at one wavelength by another; spectral subtraction; and various combinations of these mathematical techniques. Also valuable are the well-known curve fitting techniques of Savitsky-Golay and Kubelka-Munk, and N-point smoothing (signal averaging).

Other types of statistical data treatment comprise principle component analysis/regression (PCA/PCR), partial least squares (PLS), Gauss-Jordan Row reduction, etc. In these techniques, correlations are found among the constituent values of interest and one or more mathematically determined equivalent weighting constants.

By equivalent weighting constant we mean to include, among other mathematical constructions known to the art, the wavelength coefficients of multiple linear regression, the factors of partial least squares regression, the scores of principal component regression, or the constants obtained from the Gauss-Jordan Row reduction algorithm. (See Harald Martens and Tormod Naes, Multivariate Calibration, John Wiley & Sons; New York, 1989 [ISBN 471–90979–3], and Honigs, D. E., Heiftje, G. M.; Hirschfeld, T., Applied Spectroscopy, 38(3), 1984, p. 317.) Also any constant obtained from any statistical calibration could be used to calculate values for unknown samples.

Examples 7 and 9 use multiple linear regression and Examples 8 and 10 use partial least squares.

II. Utility of the Invention

This invention will find its greatest application in the petroleum refining industry and can be used to monitor the amounts of individual aromatic species in gasoline and middle distillate fuels (e.g., benzene content of gasoline).

Another preferred application is to feed the maximum allowable benzene content for reformulated fuel regulations into gasoline blending systems using a blending program such as Ashland Petroleum's BOSS Blend Optimization and Scheduling System, Chevon's GINO (Gasoline In-Line Optimization), Oil Systems, Inc. MG Blend, or other similar blending optimization programs. Other applications of the invention include various catalytic processes, such as catalytic reforming, where a knowledge of feedstock composition and product composition is preferably used to determine reactor severity, e.g., the hydrogen uptake, temperature, pressure or unit space velocity in the reforming zone. Moreover, the same analysis can be used to predict octane from the reforming step in any of the various modes of octane measurement: pump octane, motor octane, or research octane.

Example 1 shows a reformer operating under near infrared analysis to control the severity of the reforming (temperature, hydrogen pressure, hydrogen uptake, and/or unit space velocity) or moisture in the feed.

Catalytic isomerization is a process that improves octane number by the conversion of normal paraffins to their isomers. Catalytic isomerization is another application of the invention where a knowledge of feedstock composition and product composition is also preferably used to determine the catalyst activity, the space velocity, the reactor temperature, and the n-paraffin recycle.

Speciation of n-paraffins such as n-pentane and n-hexane can be determined in the feed and product and used to monitor conversion efficiency to isopentane and isohexanes, which results in increased octane. Process conditions can be adjusted to optimize the formation of isoparaffins in the reaction. Also, using a feed-forward control system, the optimum space velocity, and/or reactor temperature, and/or unreacted n-paraffin recycle rate can be determined. The mount of product and cracking that occurs during the reaction to form light gases can be predicted using the feed-forward NIR. A multiplexed or multistreamed on-line NIR can be configured so that the feed and product speciation and octane numbers can be determined by a single NIR which alternatively switches between the feed and product streams.

Moreover, moisture, which deactivates some catalysts, can be determined in the feed and alert the operators of this problem.

The invention can also be applied to catalytic alkylation which involves the reaction of low-molecular-weight olefins with an isoparaffin to form higher-molecular-weight isoparaffins with increased octane numbers and decreased Reid Vapor Pressure. Two commonly used alkylation processes use either sulfuric or hydrofluoric acid as catalysts. Solid acidic catalyst can also be Used. An on-line NIR with closed-loop control can be used to optimize octane and yield, and to minimize polymerization. The envisioned control system would be capable of adjusting the temperature, acid/hydrocarbon ratio, and isoparaffin/olefin ratio, based on NIR measurements in the feed or product streams.

A specific application of near-infrared, feed-forward control of alkylation can be deduced from discussions by C. J. Ryskamp, N. F. McGee and P. C. Badavas in Hydrocarbon Processing 65(11):113–118, wherein it is stated that alkylate octane number increases, and acid consumption decreases, with increasing isobutane/olefin ratio. However, there is a tradeoff in the form of higher deisobutanizer distillation costs which are the result of the increase in isobutane recycle required to increase the ratio of isobutane to olefin. Therefore, from an economic standpoint, it is often not practical to maximize the isobutane/olefin ratio, but rather to operate at an optimum ratio which can be lower than the maximum attainable ratio. Consequently, control of this parameter is of utmost importance. Calculation of the isobutane/olefin ratio requires acknowledge of the percent isobutane in the olefin charge stream, the isobutane makeup stream and the isobutane recycle stream. Gas chromatographs are often used to determine these parameters. However, as stated above, chromatography is a slow process in comparison to an on-line spectrophotometric method such as NIR. Therefore, it is advantageous to incorporate NIR according to the invention for feed-forward control in these streams.

A multiplexed or multistreamed on-line NIR can be configured so that the feed and product speciations, and octane numbers can be determined by a single NIR which alternates between the feed and product streams. The feed forward NIR can determine the purity of the olefin and isoparaffin feeds, and predict the optimum temperature, acid/hydrocarbon ratio and isoparaffin/olefin ratio, for a given acid catalyst purity and water content. At these conditions, the feed-forward NIR can predict product yields of LPG grade propane liquid, normal butane liquid, C5+ alkylate, and polymers. Finally, alkylate quality can be verified by NIR speciation in a feedback on-line mode. Discussions by G. L. Funk and J. A. Feldman in Hydrocarbon Processing 62(11): 92–95 state that octane contributions of alkylate product are open predicted by aid of an Alkylate Quality Factor which is a function of the volume fraction of isobutane in the reactor effluent and which can be calculated according to results obtained by the invention.

The invention will find many applications of hydrocarbon species analysis outside of the petroleum industry. An example is the monitoring of individual isomer concentration (e.g., ortho-xylene) during solvent purification in the chemical industry. Also, the invention can be used to monitor the purity of various streams, the concentration changes which occur during a chemical reaction, and even impurity concentration of hydrocarbon constituents.

Analytical Equipment

Near infrared (NIR) spectrometers, Fourier Transform near infrared (FTNIR) spectrometers, and modified near infrared spectrometers of conventional design may be used with the invention. Preferred modes of operation are transmission, reflectance, and transflectance. More preferred are transmission and transflectance. Most preferred is transflectance. Suitable spectrometers are the NIR System Models 5000 and 6500 (both bench top and on-line versions); LT Industries Model 1200; and the Guided Wave Model 300 Series; and the Perkin Elmer PIONIR models 1024 and 1024P. The spectrometer can be operated in a quality control lab, on a batch basis(receiving signals, e.g., by a sample feeding arrangement), or, more preferably, on a continuous basis in which the fluid to be measured flows through a cell or in which a probe immersed in the flowing fluid transmits optically through a fiber-optic cable to the spectrophotometer. The techniques for sampling, measuring, and signal processing can be conventional and are well known to those skilled in the art.

Blending Systems

Blending systems for use with the present invention to provide blends having desired species analysis can be of conventional design, usually involving the use of proportioning pumps or automatic control valves which control the addition rate for each of a series of components fed from different tanks or other sources. A computer receiving the output signal from the spectrophotometer can readily process the information to not only provide the target species analysis or octane number in the finished blended hydrocarbon, e.g., gasoline, but also to provide the target blend at minimum cost, given the relative costs and octane or species analysis enhancement values of the components being fed to the blending system.

The present invention permits the determination of species analysis components which have previously been determined only by laboratory analysis or by relatively long slow gas chromatography techniques. The invention permits this determination of different components to be made simultaneously and nearly continuously, providing on-line (or at-line) analysis without the need to return samples to control labs in refineries.

Examples of preferred blending systems include systems wherein said signal controls a fuel blending system feeding blending components having different benzene compositions into a common zone, whereby a product having a desired benzene composition is produced.

Examples of preferred systems include systems wherein the hydrocarbons being monitored are involved in a chemical reaction.

Examples of preferred systems include systems said signal is used to control the severity of said catalytic cracking step by adjusting catalyst:oil ratio, temperature, or recycle of naphtha or other cracked product.

BRIEF DESCRIPTION OF THE DRAWINGS

FIG. 8 is a typical chromatogram used for PIANO analysis of are formate by the prior art chromatographic technique, with detector signal plotted on the vertical axis as a function of time (in minutes) on the horizontal axis.

DESCRIPTION OF THE PREFERRED EMBODIMENTS

EXAMPLE 1

(Invention Controlling Fixed Bed Catalytic Reformer)

Figure 1:
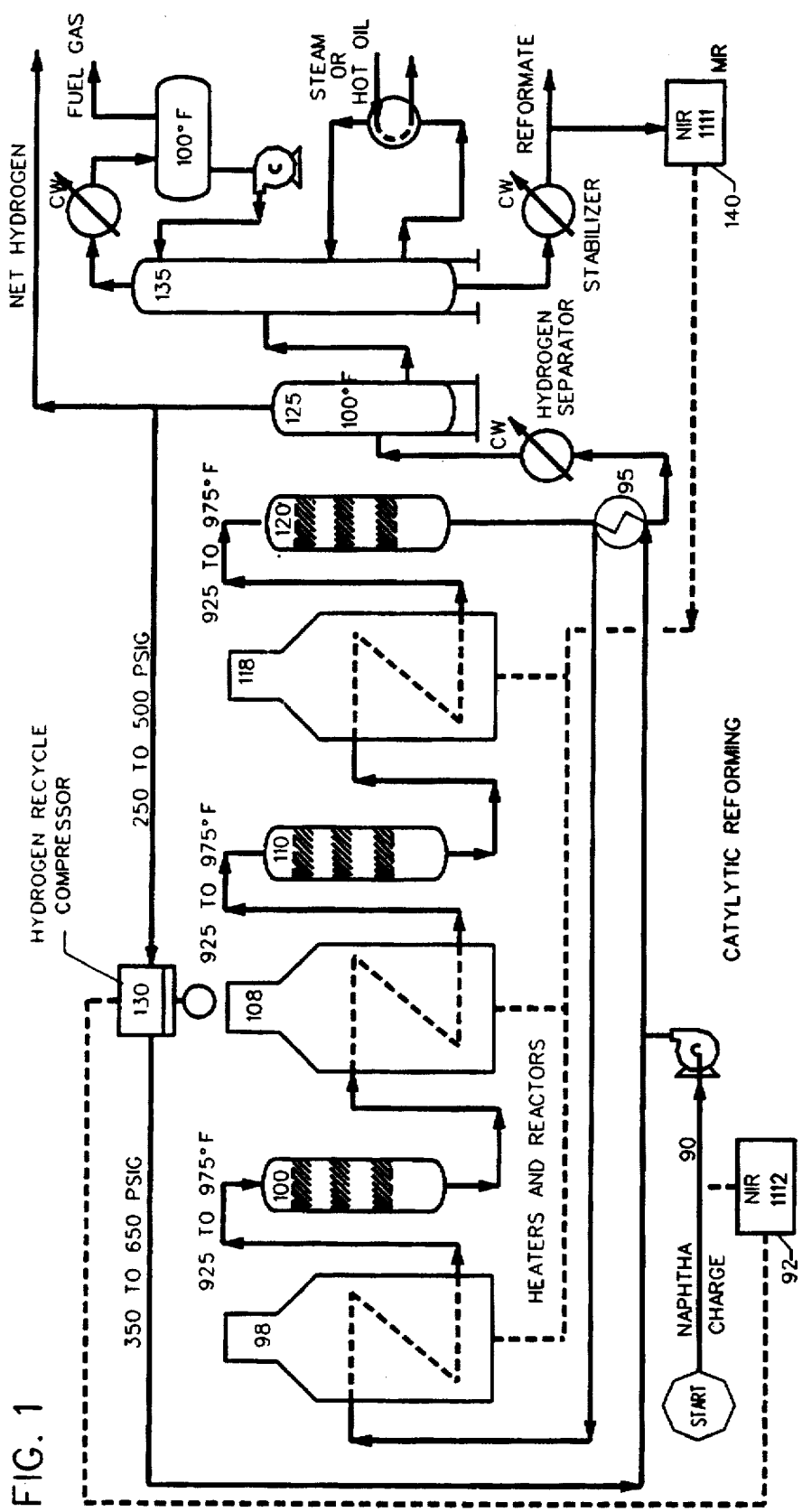
FIG. 1 is a plot of a typical catalytic reforming process, as shown in Gary and Handwerk, Petroleum Refining Marcel Dekker, third edition, 1994 with the preferred near infrared spectrometers of the present invention added to provide control to the heaters and/or the hydrogen recycle compressor.

FIG. 1 shows schematically the process flow of a typical semi-regenerative catalytic reforming unit. Fixed-bed reforming units containing typical reforming catalysts are shown in series as 100, 110 and 120. The operation of the unit is generally as described in Gary and Handwerk, Petroleum Refining, under catalytic reforming and isomerization.

Referring to FIG. 1, naphtha charge 90 is pumped through economizing heat exchanger 95 into heater 98 which heats it in the range of 496°–524° C. (925°–975° F.) and conducts it to a first fixed bed reforming unit 100 which contains a conventional reforming catalyst of the platinum products from reformer 100 moves sequentially through heater 108 and reformer 110 and heater 118 and reformer 120. The reformed product moves on to hydrogen separator 125 and fractionating column 135 which produces as bottoms a reformate stream high in aromatics. Hydrogen recycle compressor 130 compresses hydrogen from hydrogen separator 125 to feed hydrogen to mix with the naphtha charge 90 under varying pressures and throughputs of hydrogen.

According to the invention, an NIR analyzer 140 samples the effluent from the reformer, analyzes it based on calibrations shown in Table A, which sets forth for each specie, the constants k(0), k(1), k(2), k(3), in the equation below and the wavelengths at which absorption is measured together with the correlation, R and the NIR standard error of estimate as compared to the primary method shown:
Concentration of Species=

$$k(0)+k(1)\times(d^2A/d\lambda^2)_{\lambda_1}+k(2)\times(d^2A/d\lambda^2)_{\lambda_2}+k(3)\times(d^2A/d\lambda^2)_{\lambda_3}$$

Where k(0)=bias coefficient
k(n)=coefficient for wavelength $\lambda$n
$(d^2A/d\lambda^2)_{\lambda,n}$=second derivative of absorbance at wavelength $\lambda$n for n=1, 2 and 3 (wavelengths $\lambda 1$, $\lambda 2$, and $\lambda 3$)

The purpose of reforming is primarily to manufacture aromatic species. Therefore, the lower the aromatics content analyzed by NIR instrument 140, the higher the temperature of heaters 98, 108 and 118 must be to increase the "severity" of the reforming process, and thereby to increase the aromatics in the product stream being measured by NIR 140. Isomerization and thermal cracking can both occur to some degree during reforming. NIR 140 can also be used to measure the degree of isomerization as determined by the isoparaffin content and the degree of cracking as determined by olefin content.

According to the invention, a near-infrared (NIR) instrument 140 with closed-loop control capability and operating according to the techniques described above, is placed "at line" so that it measures a portion of the reformate product, analyzes it for aromatics and/or octane or other parameter. Noting any differences between the measured value and the preset desired value, the NIR, closed-loop control unit 140 sends a signal to the heaters 98, 108, and 118 to increase or decrease their temperature or the temperature of any one of them. By increasing the temperature, the "severity" of the reforming process is increased which tends to increase the aromatics and/or octane number of the finished reformate product being measured by the NIR unit 140. Alternatively, (or additionally) the signal from NIR unit 140 can be sent to the hydrogen recycle compressor 130 which increases the pressure of hydrogen in the feed, thus increasing the hydrogen uptake during the reforming process. This serves to reduce the amount of aromatics in the reformate product.

Similarly, NIR instrument 140 may additionally control hydrogen recycle compressor 130 to adjust the hydrogen pressure as needed to increase the aromatics in the reformate product from the reforming unit.

Finally, NIR instrument 140 can be used to monitor catalyst performance as determined by product composition at a given severity.

Additionally, or alternatively, a different NIR instrument 92 (or the same NIR instrument 140 multiplexed for either multistreaming or multiplexing with fiber optics so as to analyze both the naphtha charge 90 and the reformate product), measures the naphtha charge and by "feed forward" predicts the temperature and hydrogen pressure which will be needed for heaters 98, 108 and 118, and hydrogen recycle compressor 130 in order to provide the desired product yield and level of aromatics in the reformate product being analyzed.

As an additional precaution, the NIR units can also analyze for H$_2$O to determine the presents presence of deleterious moisture which can otherwise deactivate the reformer catalysts in reformer units 100, 110 and 120.

By the use of the invention, the aromatics species and/or octane number of the reformate can be controlled more closely than with similar methods employing gas chromatography because the NIR instrument 140 and/or 92 can analyze and respond in less than about one minute, providing close control and fast response. If a specific aromatic species such as benzene is especially desired to be increased or minimized in the reformate product, that specific species can be measured by the techniques described above, the measured value then compared with the preset desired value and the corresponding signal sent to the heaters and/or hydrogen compressor.

Similarly, space velocity can be increased in response to the NIR unit signal in order to reduce the severity of the reforming operation and reduce the aromatics in the produced reformate.

EXAMPLE 2

(Invention Controlling A Continuous Catalytic Reformer)

Figure 2:
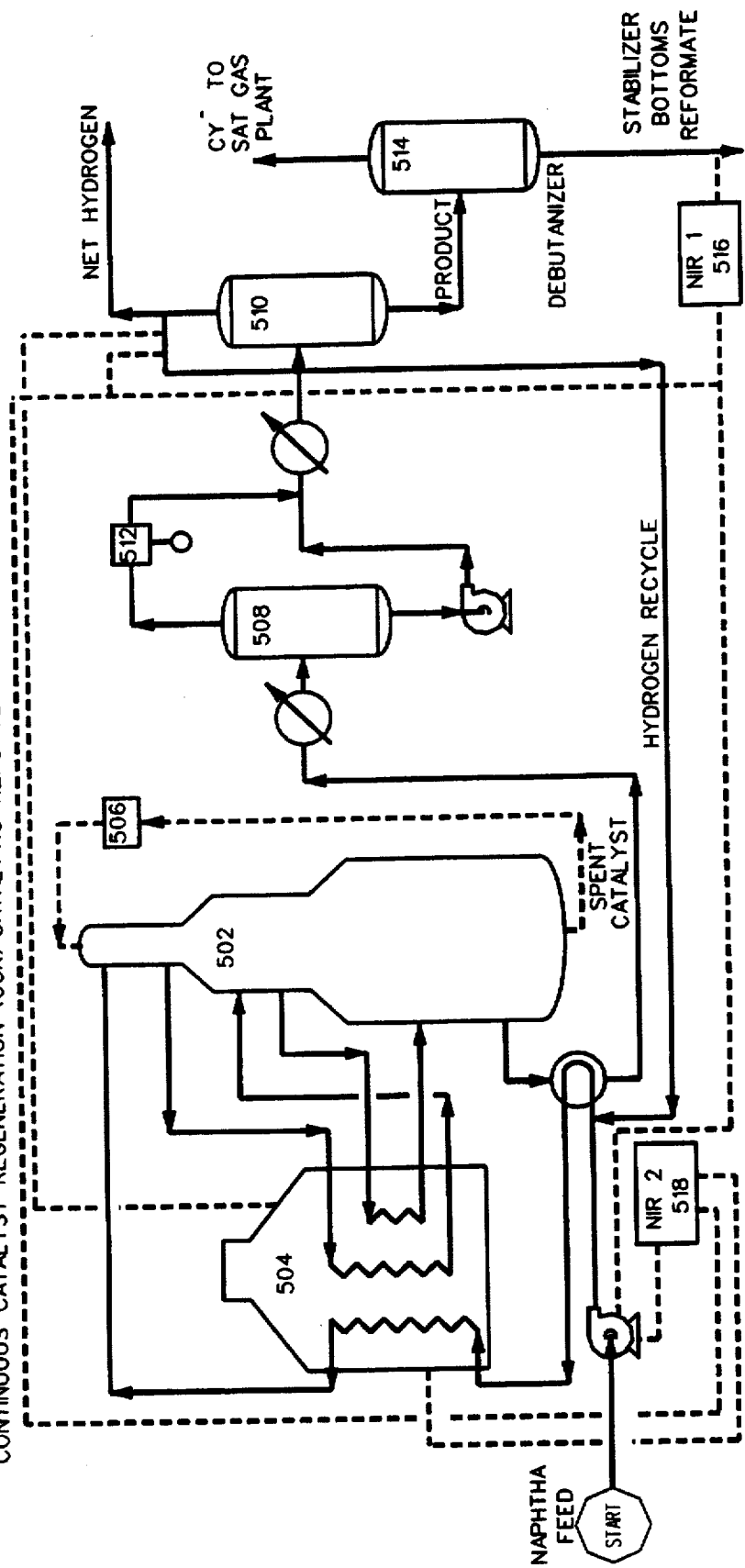
FIG. 2 is a diagram of a control system for a continuous catalytic reformer, another typical reforming step process in a refinery, as shown in Gary and Handwerk, Petroleum Refining Marcel Dekker, third edition, 1994; with feed-forward and feedback, near-infrared control.

FIG. 2 is a diagram of a control system for a continuous catalytic reformer with both feed-forward and feedback, near-infrared (NIR) control.

A UOP-type continuous catalytic reformer (CCR) unit is controlled by the NIR instruments of the present invention. In FIG. 2, R is the reactor, H is the heater, RS is the catalytic regeneration section, LPS is the low pressure separator, HPS is the high pressure separator, C is the hydrogen compressor, and DBU is the debutanizer.

Naphtha feed is pumped through heater H and then to reactor R which contains recirculating catalyst. Regenerator RS continuously regenerates the catalyst by burning off carbon, reducing and acidifying the catalyst, and then returning it to the top of reactor R. The product is removed from reactor R to low-pressure separator LPS which removes hydrogen from the product. The removed hydrogen is compressed by hydrogen compressor C. The product is then directed to high-pressure separator HPS which removes additional hydrogen, a portion of which is recombined with the naphtha feed. Product from high-pressure separator HPS is directed to debutanizer DBU which removes butane and lighter hydrocarbons. The bottom fraction from debutanizer DBU is sampled and analyzed by feedback analyzer NIR1 which in turn is used in a feedback mode to control the feed rate, the temperature of heater H and the hydrogen recycle from high-pressure separator HPS.

Feed-forward NIR analyzer NIR2 is also used to sample the naphtha feed for control of the feed rate, the temperature of heater H and the hydrogen recycle from high-pressure separator HPS. By use of feed-forward control in this configuration, the severity of the reforming process is adjusted based on the concentrations of aromatic-forming species (such as naphthenes) in the feeds. In this way, aromatics in the product is controlled based on the chemical properties of the feedstocks. In addition, feed-forward NIR analyzer NIR2 alerts the operator to excessive amounts of undesirable species in the feed.

Figure 3:
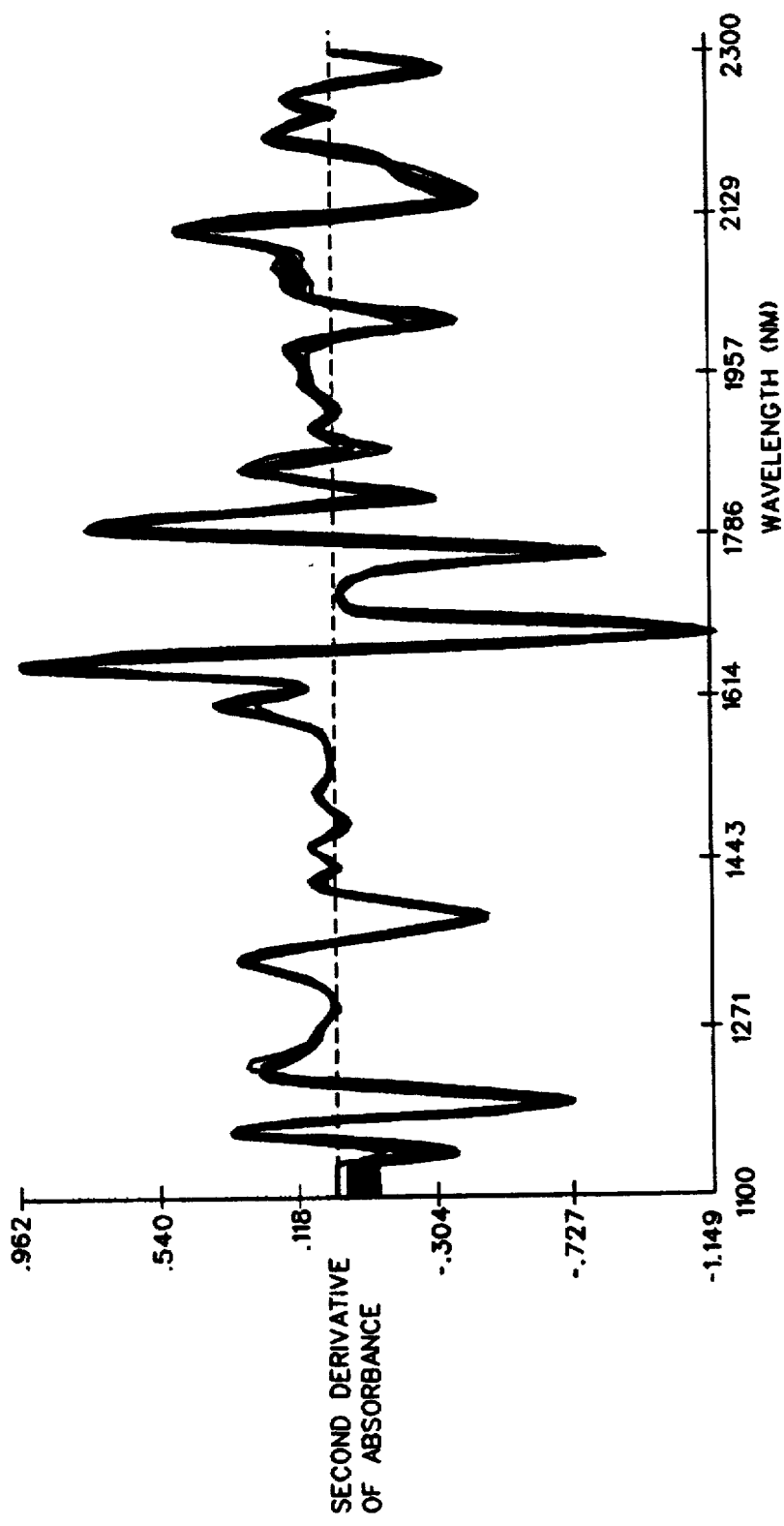
FIG. 3 is a plot of the second derivative spectrum across the NIR range 1000 to 2500 nm for 52 reformate sample prepared according to Example 1.

NIR2 may be the same instrument as NIR1 or a different NIR instrument, with feed-forward and feedback functions operating in a multiplexing or multistreaming mode. According to the invention, NIR analyzers NIR1 and NIR2 sample the feed and the stabilizer bottoms, and analyze them based on calibrations such as those shown in Table A, which sets forth the constants k(0), k(1), k(2), k(3), and the wavelengths at which absorption is measured together with the correlation, R and the NIR standard error of estimate as compared to the primary method shown. FIG. 3 shows typical second-derivative spectra used for calibrations such as those shown in Table A.

Typical analyses of reformate are shown in Table B, with comparison of the NIR results with results by the primary method (GC-PIANO).

EXAMPLE 3

(Invention Controlling a Fuel Blender)

Figure 4:
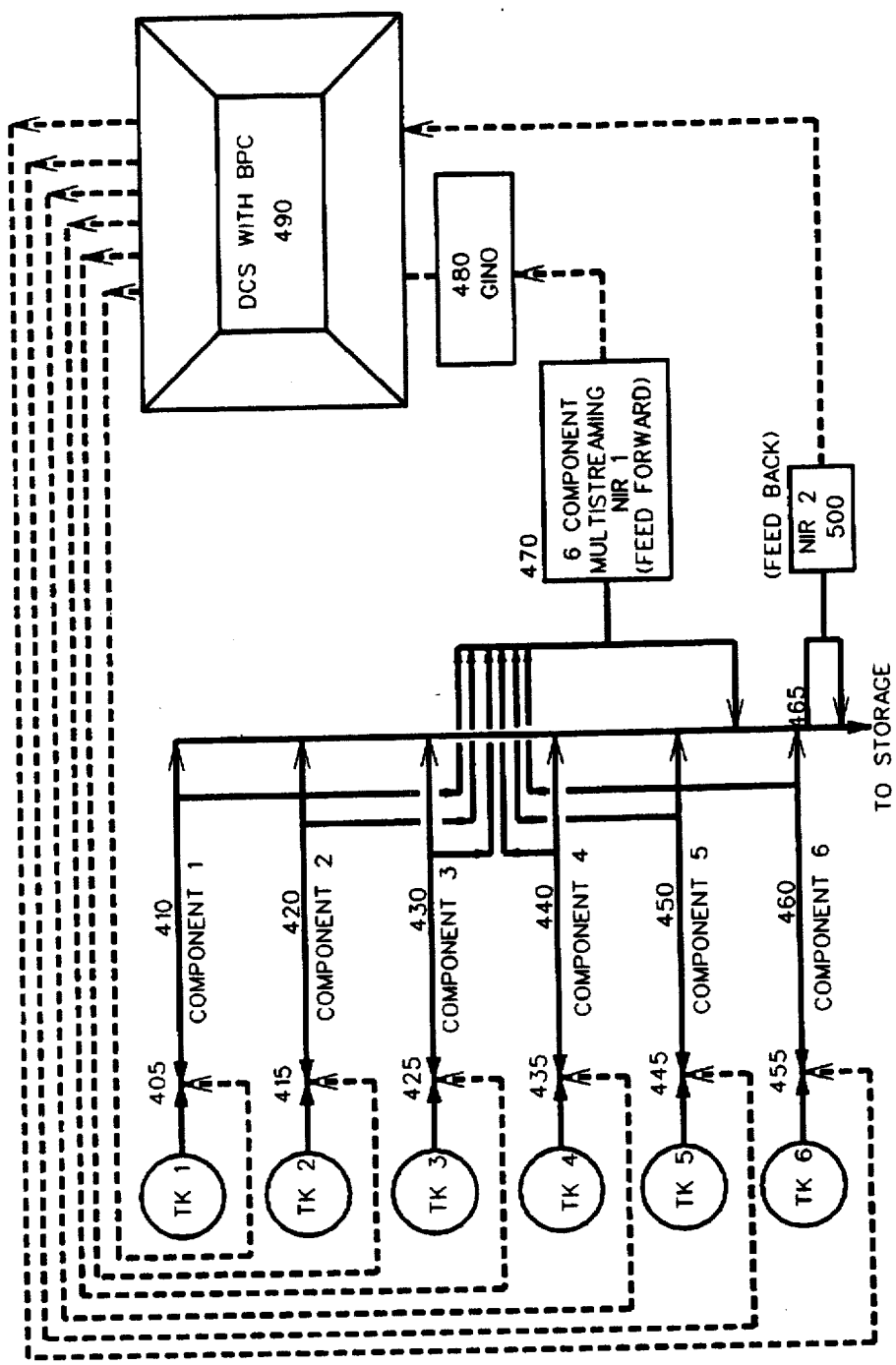
FIG. 4 is a control diagram for a typical on-line blender in a refinery with both feed-forward and feedback, near-infrared (NIR) control, as described by W. T. Welch in the Proceedings of the National. Petroleum Refiners Association (NPRA), National Fuels and Lubricants Meeting, FL-93-114, 1993.

FIG. 4 is a control diagram for a typical on-line blender in a refinery, with both feed-forward and feedback, near-infrared (NIR) control.

In FIG. 4, the use of multistreaming, whereby the component streams are switched sequentially to a single probe using valves, is illustrated; however, multiplexing, whereby a probe is located at each control point; or a combination of both; can also be used. In a multistreaming operation such as that illustrated in FIG. 4, components 410, 420, 430, 440, 450 and 460 are sequentially routed to the sample cell or sample probe of NIR 470 which analyzes each stream for properties or components of interest (e.g., benzene). A signal for each stream (proportional to vol % benzene) is then transmitted to optimizing software such as GINO. The GINO software, resident in blending computer 480, then continuously optimize and update the blend recipe, then downloads the updated recipe to Blend Ratio Control (BRC) software which is resident in Distributed Control System (DCS) 490. The BRC software is capable of controlling DCS 490 which in turn adjusts the position of valves 405, 415, 425, 415, 445, and 455 to change the flow rates of components 410, 420, 430, 440, 450 and 460, respectively.

Another NIR 500 can also be used in a feedback mode. A slip stream 465 of the fin/shed blend is directed to the sample probe or sample cell of NIR 500, which analyzes the finished blend for benzene and other properties of interest. DCS 490 then receives the feedback signal from NIR 500 in the same manner as it receives the feed-forward signals from NIR 470. The DCS 490 is configured to allow direct control of valves 405, 415, 425, 435, 445 and 455 by the feedback control loop to override the recipe established by the feed-forward control loop when necessary.

NIR 500 may be the same instrument as NIR 470, with feed-forward and feedback functions operating in a multiplexing or multistreaming mode.

EXAMPLE 4

(Invention Controlling an Isomerization Unit with Pentane Recycle)

Figure 5:
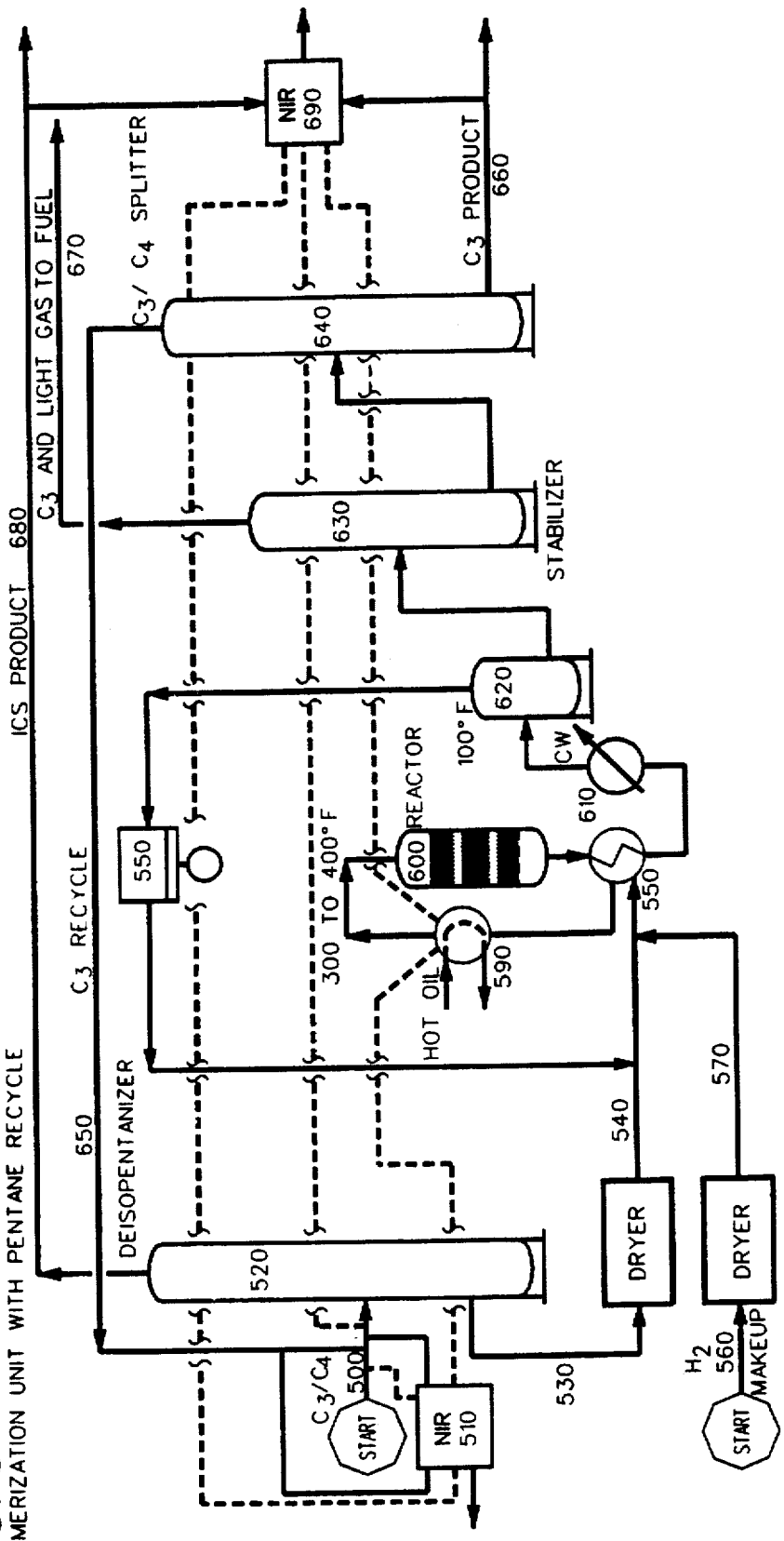
FIG. 5 is a control diagram of a typical isomerization unit in a refinery as shown in Gary and Handwerk, Petroleum Refining, Marcel Dekker, third edition, 1994; with both feed-forward and feedback, near-infrared control.

FIG. 5 is a control diagram of a typical isomerization unit in a refinery, with near-infrared control having both feed-forward and feedback control.

In FIG. 5, the feed stream 500 first goes to deisopentanizer 520 which removes the low-boiling isopentane product 680 as the overhead fraction. The bottom fraction 530 is then directed to dryer 540 combined with recycle hydrogen 550, to which makeup hydrogen 560 is added from dryer 570 as needed. The combined stream is directed through economizing heat exchanger 580 to heater 590, then to reactor 600, then to water cooler 610 and then to hydrogen separator 620 for separation of recycle hydrogen 550 from the product stream, which is then directed to stabilizer 630. Propane and light gases are removed from stabilizer 630 as the overhead fraction 670. The bottoms from stabilizer 630 are then directed to splitter 640 for separation of pentanes 650 as the overhead fraction, from product hexanes 660 which are removed as the bottom fraction. Pentanes 650 are recycled to deisopentanizer 520.

Feed-forward control is accomplished by the use of NIR 510 to analyze feed 500, recycle pentanes 650 and/or the combined stream composed of both. Use of NIR 510 to speciate paraffins in these streams, more preferably pentanes and hexanes, can provide the refiner with important real-time information for optimization of reactor temperature, feed rate and recycle rate.

Feedback control is typically accomplished for both product hexanes 660 and isopentane product 680 by NIR 690. By tracking the amounts of unreacted normal hexanes in product hexanes 660 and unreacted normal pentane in isopentane product 680, product quality is continuously monitored.

Similar to the blender operation, the feedback control loop is configured with capability to override the feed-forward control loop.

NIR 510 may be the same instrument as NIR 690, with feed-forward and feedback functions operating in a multiplexing or multistreaming mode.

EXAMPLE 5

(Invention Controlling a Hydrogen Fluoride (HF) Alkylation Unit)

Figure 6:
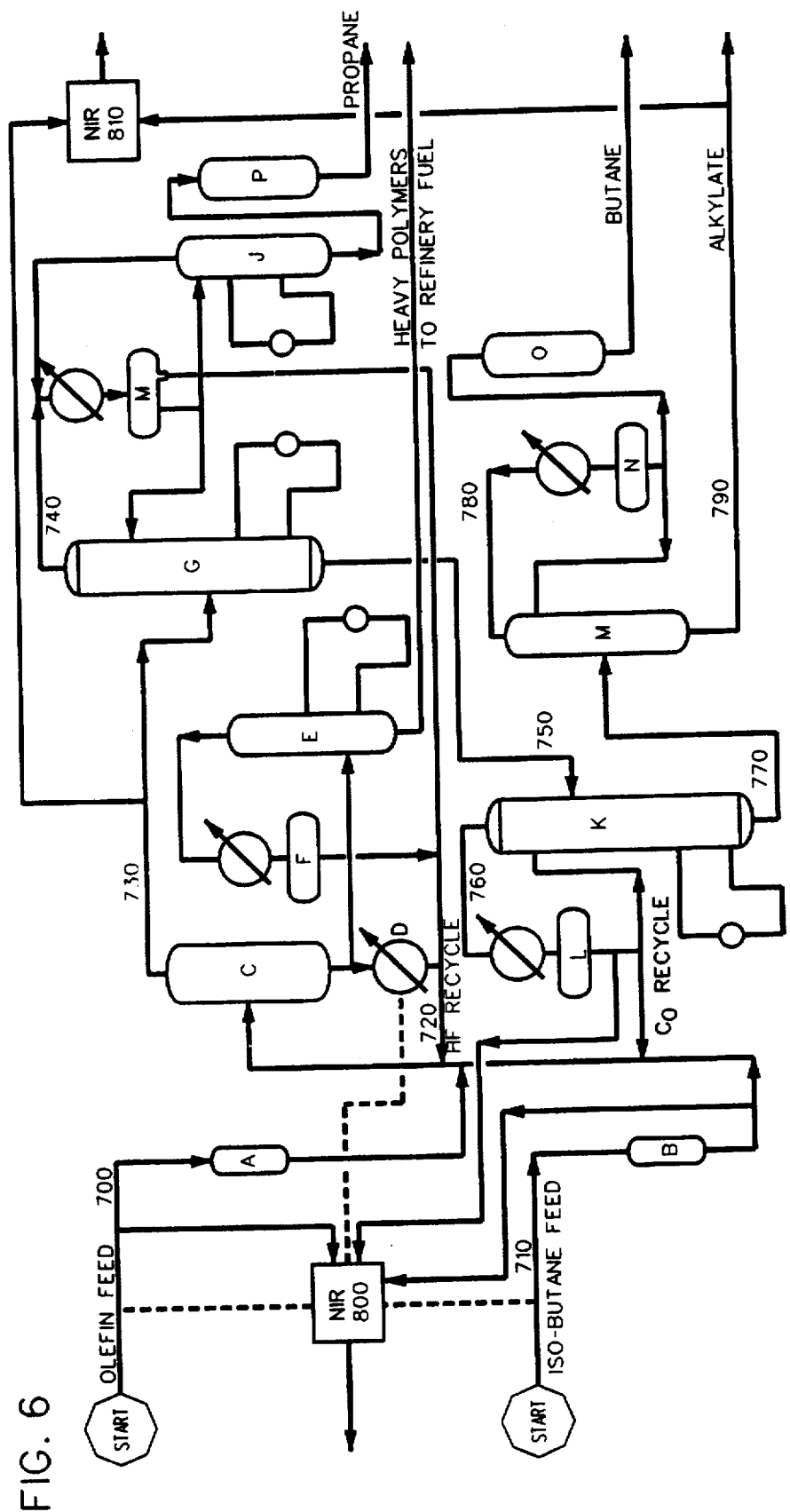
FIG. 6 is a control diagram of a typical hydrogen fluoride (HF) alkylation unit in a refinery, as shown in Gary and Handwerk, Petroleum Refining, Marcel Dekker, third edition, 1994; with both feed-forward and feedback, near-infrared control.

FIG. 6 is a control diagram of a typical hydrogen fluoride (HF) alkylation unit in a refinery, with both feed-forward and feedback near-infrared control.

In FIG. 6, olefin feed 700 and isobutane feed 710 are directed through dryers A and B, respectively, combined with each other and then with HF acid recycle 720 before reaching acid settler C, which disengages the hydrocarbon overhead fraction 730 and immediately recycles the acid 720 through acid cooler D. Overhead fraction 730 arrives at depropanizer G which removes propane 740 as the overhead fraction and directs it to propane accumulator H, from which any remaining HF is removed in stripper J and propane caustic treater P. The bottom fraction 750 from depropanizer G is directed to deisobutanizer accumulator K, which separates this stream into isobutane overhead fraction 760 and bottom fraction 770. Isobutane 760 is recycled and combined with feed streams 700 and 710. The bottom fraction 770 is then directed to debutanizer M which removes n-butane 780 as overhead from alkylate bottom fraction 790.

Feed-forward control of the isobutane/olefin ratio is accomplished by sampling olefin feed stream 700, isobutane feed or makeup stream 710 and isobutane recycle stream. The three streams are directed to NIR 800 in a multistreaming mode, or, alternatively, sampled using separate probes or flow cells in a multiplexing mode. NIR 800 the analyzes the streams for percent isobutane. This value, in combination with flow measurements and the predetermined optimum isobutane/olefin ratio, allows calculation of the flow rate of olefin feed stream 700 required to maintain the desired ratio.

Feed-forward control of temperature, acid/hydrocarbon ratio and isoparaffin/olefin ratio can also be accomplished by using the NIR values for percent isobutane in olefin feed 700 and isobutane feed 710 as previously mentioned.

Feedback control can involve the determination of the composition of the isobutane content in hydrocarbon overhead 730 from reactor C as well as the composition of alkylate product 790. The percent isobutane in hydrocarbon overhead 730 is used to calculate the previously-mentioned quality factor which is used to predict the contribution of the alkylate product 790 to octane numbers in blends.

NIR 800 may be the same instrument as NIR 810, with feed-forward and feedback functions operating in a multiplexing or multistreaming mode.

EXAMPLE 6

Invention Controlling a Methyl Tertiary Butyl Ether (MTBE) Unit

Figure 7:
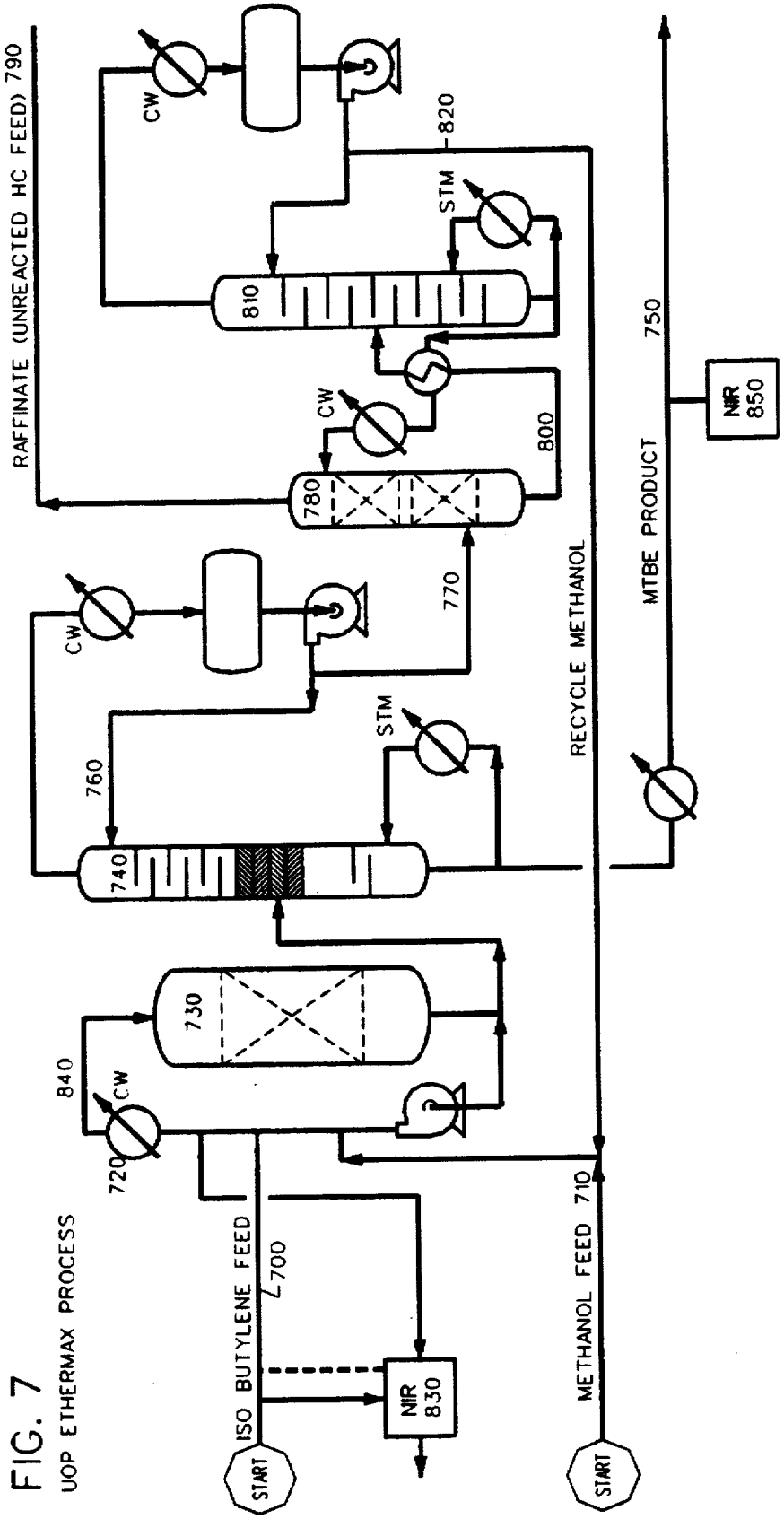
FIG. 7 is a control diagram of a typical methyl tert-butyl ether (MTBE) unit in a refinery as shown in Gary and Handwerk, Petroleum Refining, Marcel Dekker, third edition, 1994; with feed-forward, near-infrared control.

FIG. 7 is a control diagram of a typical methyl tert-butyl ether (MTBE) unit in a refinery, with both feed-forward and feedback near-infrared control. A useful application of on-line feed-forward control involves a critical calculation of Isobutylene to methanol ratio.

Referring to FIG. 7, a UOP design, excess methanol is used to obtain almost complete conversion of the isobutylene. Isobutylene feed 700 and methanol feed 710 are combined with recycle methanol 820 and directed through cooler 720 to the top of primary reactor 730. Most of the effluent from reactor 730 is recycled but a small amount is directed to proprietary (Koch Engineering) Reaction with Distillation (RWD) column 740 which contains a catalyst section just above the feed inlet and serves as a secondary reactor. MTBE product 750 is withdrawn from the bottom of RWD column 740. Unreacted methanol and isobutylene pass through the catalyst-containing section of RWD column 740 and are convened to additional MTBE which also withdrawn from the bottom. The overhead fraction of RWD column 740, consisting mostly of unreacted methanol vapor and butanes from feed stream 700, is split into recycle stream 760 and methanol recovery stream 770. Methanol is extracted with water from recovery stream 770 in water wash column 780. Raffinate 790, consisting mainly of unreacted butanes, is used as feed for other processes. Extract 800 is distilled in tower 810, the water being recycled to wash column 780 and the distilled methanol directed to recycle methanol stream 820.

NIR 830 is used in a feed-forward control loop to monitor the composition of isobutylene feed 700 the combined isobutylene/methanol stream being fed to primary reactor 730. By measuring flow rates, the amounts of butanes, butenes and isobutylenes in isobutylene feed stream 700, and percent methanol and isobutylene in combined stream 840, the methanol/isobutylene ratio can be calculated and used to control the flow of isobutylene. The methanol/isobutylene ratio is a critical parameter in this process because it is desirable to use a small excess of methanol.

MTBE purity can be monitored using NIR 850. NIR 830 and NIR 850 can be a single instrument in a multiplexing or multistreaming mode. Other ether manufacturing steps (TAME, ETBE, diisopropyl, ether, etc.) can be similarly controlled.

EXAMPLE 7

(Speciation of Aromatics For Reformer Control According to the Invention Using MLR)

Fifty-two samples of hydrocarbons are used for calibration according to the techniques of the present invention. Calibration results are shown in Table A, for PIANO and for speciation of individual compounds. Debutanizer bottoms, obtained from the bottom of the fractionating tower which removes components lighter than butane as overheads, are used as calibration samples. All samples are analyzed by gas liquid chromatography by a procedure taught by Analytical Automation Specialists, Inc., "The Detailed Analysis of Petroleum Naphthas, Reformates, Gasoline and Condensates by High-Resolution Gas chromatography", operators manual, P.O. Box 80653, Baton Rouge, La. 70898, with results as shown in Table G.

The NIR instrument used for the invention is was an NIRSystems on-line Model 5000, near infrared spectrophotometer measuring all of the 52 samples. Wavelengths used and the range of volume percents is shown in Table A. The samples were selected so as to represent an increasing concentration of each of the species or components so that the entire range was covered.

A multiple linear regression analysis was performed on the second derivative of the absorbances measured at the indicated wavelengths. Also shown in Table A are the regression coefficients, the multiple coefficients of correlation, and the standard errors of the estimate (calculated for this calibration set by conventional well-known statistical techniques).

Nine samples are used as a prediction set for prediction of species and component concentrations in unknown samples. Again, the second derivatives of the absorbances are used as the independent variables in the multiple linear regression equations obtained from the calibration set. Results are shown in Table B. The NIRSystems computer program supplied with the apparatus (NIR Spectral Analysis Software) was used for multiple regression analysis, although SAS or another well-known statistical program could be used as well. These programs multiply the second derivative of each absorbance at each wavelength by its respective weighting constant, then sum the products to provide a weighted value which is characteristic of the predicted percent of each respective species or component. It can be seen that the actual standard error of prediction shows excellent correlation between the model and the actual concentrations in samples not in the calibration set.

Table B (reformate) shows that the invention measures concentration of species with accuracy comparable to the slow GC PIANO method, but at much faster control response times.

EXAMPLE 8

(The Invention Using Species Analysis and Partial Least Squares)

The same 52 samples analyzed in Example 6 with multiple linear regression (MLR) results shown in Table B, were reprocessed using partial least squares regression equations (PLS). Results are shown in Table C for each species commonly requiring analysis in refinery practices. As shown under column "R", the correlation coefficients are as good or better than those obtained according to the invention using the multiple linear regression (Example 7, Table A). NIR values for all of the constituents approach the accuracy of the primary method, GC PIANO, while avoiding the man-hour requirements and delayed control response of the GC PIANO analysis. In general, GC PIANO requires approximately 3–4 hours for an analysis while an on-line NIR analysis of the same constituents with automatic input to a conventional Distributed Control System (DCS) or similar control device; requires only about thirty seconds. Thus the invention provides a substantially faster control response.

EXAMPLE 9

(Speciation of Aromatics For Blender Control Using Multiple Linear Regression According to the Invention)

One hundred forty-three samples of hydrocarbons are used for calibration according to the techniques of the present invention. Calibration results are shown in Table D, for PIANO and for speciation of individual aromatic compounds. All samples are analyzed by gas liquid chromatography by a procedure taught by Analytical Automation Specialists, Inc., "The Detailed Analysis of Petroleum Naphthas, Reformates, Gasoline and Condensates by High-Resolution Gas chromatography", operators manual, P.O. Box 80653, Baton Rouge, La. 70898, with typical results as shown in Table H.

The instrument used for this example of the invention is a Perkin Elmer PIONIR 1024P, near infrared spectrophotometer measuring all of the samples. Wavelengths used and the range of volume percents is shown in Table D. The samples are selected so as to represent an increasing concentration of each of the species or components so that the entire range was covered.

A multiple linear regression analysis was performed on the second derivative of the absorbances measured at the indicated wavelengths. Also shown in Table D are the regression coefficients, the multiple coefficients of correlation, and the standard errors of the estimate (calculated for this calibration set by conventional well-known statistical techniques).

EXAMPLE 10

(Speciation of Aromatics For Blender Control Using Partial Least Squares According to the Invention)

One hundred thirty-four samples analyzed in Example 9 with multiple linear regression (MLR) results shown in Table D, were reprocessed using partial least squares regression equations (PLS). Results are shown in Table E for each species commonly requiring analysis in refinery practices. As shown under column "R", the correlation coefficients are as good or better than those obtained according to the invention using the multiple linear regression (Example 9, Table D). NIR values for all of the constituents approach the accuracy of the primary method GC PIANO, while avoiding the man-hour requirements of the GC PIANO analysis. In general, GC PIANO requires approximately 3–4 hours for an analysis. On the other hand, an on-line NIR analysis of the same constituents with automatic input to a DCS or similar control device, requires only about thirty seconds. Thus the invention provides a substantially faster control response.

Nine samples were used as a prediction set for prediction of species and component concentrations in unknown samples. Again, the second derivatives of the absorbances are used as the independent variables in the PLS regression equations obtained from the calibration set. Results are shown in Table F. The NIRSystems computer program was used for partial least squares analysis, although SAS or another well-known statistical program could be used as well. It can be seen that the actual standard error of prediction shows excellent correlation between the model and the actual concentrations in samples not in the calibration set.

Table F (gasoline) shows that the invention measures concentration of species with accuracy comparable to the slow GC PIANO method by a much faster control response time.

EXAMPLE 11

(Comparative with Species Analysis Using Conventional Gas Liquid Chromatography)

Table H is a typical PIANO analysis report as performed using PIANO Software Version 6.06 Serial Number P-0182U (Analytical Automation Specialists, Inc.) The chromatogram for a reformate, shown in FIG. 8, was obtained using a Hewlett-Packard Model 5890 temperature-programmed gas chromatograph with a flame ionization detector and a Supelco Petrocol DH capillary column (fused silica, 100M×0.25 mm i.d., df=0.5 uM). Chromatographic conditions were adjusted according to the standard methods established by the instrument manufacturer and Analytical Automation Specialists, Inc. Table H contains detailed speciation of many paraffins, isoparaffins, aromatics, naphthenes and olefins by this method. Thus it is seen that this prior art method is useful for the determination of individual species as well as compound types, and can serve as the primary method for calibration of the near-infrared instruments used in the present invention. However, as shown in FIG. 8, this method is slow. FIG. 8 shows an elutriation time for the last fractions of 142 min or over two hours. The PIANO method is thus seen to be too slow for efficient use in closed-loop control for many refinery processes.

Modifications

Specific compositions, methods, or embodiments discussed are intended to be only illustrative of the invention disclosed by this specification. Variation on these compositions, methods, or embodiments are readily apparent to a person of skill in the art based upon the teachings of this specification and are therefore intended to be included as part of the inventions disclosed herein. For example, FTNIR or even Raman IR can be used in place of NIR by conventionally modifying the mathematical conversions and data analysis, so that spectral data obtained by FTNIR or Raman IR are used in place of the near infrared spectral data, and calibrating using one or more mathematical methods as explained above, against the PIANO analysis or other primary method as with an NIR instrument.

Reference to [documents] U.S. patents made in the specification is intended to result in such patents [or literature].

TABLE A

Multiple Regression Equations for Reformate using Second Derivative Data in the 1100–2500 nm Range

| Compound Volume % | Primary Method | Range | Average | Constants | | | | | Wavelengths (nm) | | | R | 2 R | NIR STD ERROR |
|---|---|---|---|---|---|---|---|---|---|---|---|---|---|---|
| | | | | k(0) | k(1) | k(2) | k(3) | 1 | 2 | 3 | | | | |
| Total Aromatics | GC-PIANO | 35.917–68.001 | 59.758 | 79.902 | 93.863 | 82.716 | −105.131 | 1834 methylene | 1624 aromatic | 1232 methyne:t-butyl or methylene | 0.999 | 0.998 | 0.302 |
| Benzene | GC-PIANO | 2.697–5.730 | 4.394 | 19.610 | −12.233 | −75.612 | 21.631 | 2128 aromatic | 1624 aromatic | 1834 methylene | 0.995 | 0.989 | 0.0675 |
| Toluene | GC-PIANO | 8.770–16.169 | 13.633 | 11.905 | −39.118 | 86.410 | −144.518 | 1650 aromatic | 1796 methylene | 1224 methyne | 0.992 | 0.983 | 0.218 |
| Total Xylenes | GC-PIANO | 8.512–19.999 | 15.596 | −108.345 | 901.434 | 203.014 | 488.084 | 1458 methylene | 2028 methyl | 1622 aromatic | 0.989 | 0.978 | 0.422 |
| m-Xylene | GC-PIANO | 4.013–9.572 | 7.657 | 51.160 | −57.877 | −476.542 | −53.513 | 1648 aromatic | 1504 methyl | 1400 aromatic | 0.978 | 0.956 | 0.276 |
| p-Xylene | GC-PIANO | 1.802–4.034 | 3.258 | 12.589 | 32.439 | 111.426 | −21.007 | 1204 methyl | 1356 methyl | 1646 methyl | 0.984 | 0.967 | 0.098 |
| o-Xylene | GC-PIANO | 2.697–6.393 | 5.005 | 24.885 | −46.606 | −28.127 | −47.216 | 2148 aromatic | 1854 methylene | 1646 aromatic | 0.986 | 0.971 | 0.178 |
| Ethyl-Benzene | GC-PIANO | 2.292–3.960 | 3.259 | 18.684 | −13.659 | −18.225 | −23.611 methyl | 1176 aromatic | 1642 methyne:t-butyl | 1230 aromatic | 0.983 | 0.966 | 0.087 |
| n-Propylbenzene | GC-PIANO | 0.832–1.297 | 1.113 | 6.223 | −99.616 | −7.656 | 24.658 | 1466 | 1204 methyl | or methylene 1408 methyl | 0.967 | 0.936 | 0.034 |
| Total Xylenes + Ethyl-Benzene | GC-PIANO | 10.804–23.959 | 18.855 | 152.836 | 239.466 | −348.026 | 71.360 | 1196 methylene | 2232 | 1800 | 0.990 | 0.980 | 0.475 |
| BTX | GC-PIANO | 19.979–40.253 | 33.623 | 81.849 | −196.094 | 84.458 | methyl −114.177 methyne:t-butyl or methylene | 1230 methyl | methylene 1792 methylene | 1642 aromatic | 0.996 | 0.992 | 0.423 |
| BTEX | GC-PIANO | 22.271–44.213 | 36.882 | 95.748 | 84.555 | −211.572 | −128.650 | 1792 methylene | 1230 methyne:t-butyl or methylene | 1642 aromatic | 0.993 | 0.985 | 0.637 |
| Olefins | GC-PIANO | 0.464–1.697 | 1.083 | −3.051 | 134.146 | 24.440 | 104.801 | 1612 olefin | 1200 methyl | 1140 aromatic | 0.978 | 0.957 | 0.052 |
| Paraffins | GC-PIANO | 8.355–22.359 | 11.084 | −50.245 | 217.444 | −147.095 | 264.005 | 1976 (1) | 2062 (1) | 1232 methyne:t-butyl or methylene | 0.997 | 0.993 | 0.235 |
| n-Pentane | GC-PIANO | 0.685–4.823 | 1.818 | −55.911 | 61.895 | −418.774 | 280.953 | 1650 aromatic | 1452 methylene | 1970 (1) | 0.931 | 0.867 | 0.338 |
| n-Hexane | GC-PIANO | 2.673–5.185 | 3.527 | 4.362 | −25.343 | −30.921 | −53.680 | 1844 methylene | 2014 methyl | 1624 aromatic | 0.926 | 0.857 | 0.179 |
| n-Heptane | GC-PIANO | 1.612–7.484 | 2.869 | 25.158 | 28.376 | 105.983 | 235.947 | 1662 aromatic | 1184 methyl | 1418 methyl | 0.990 | 0.980 | 0.119 |
| Isoparaffins | GC-PIANO | 20.004–34.565 | 24.081 | 103.497 | −285.180 | 109.252 | −203.116 | 2084 olefin | 1938 methyl | 1230 methyne:t-butyl of methylene | 0.997 | 0.993 | 0.304 |
| Iso-Pentane | GC-PIANO | 1.058–8.247 | 2.937 | −83.412 | 444.557 | −139.031 | 404.416 | 1970 | 2144 (1) | 1484 | 0.917 | 0.840 | 0.613 |

TABLE A-continued

Multiple Regression Equations for Reformate using Second Derivative Data in the 1100–2500 nm Range

| Compound Volume % | Primary Method | Range | Average | Constants | | | | Wavelengths (nm) | | | R | R² | NIR STD ERROR |
|---|---|---|---|---|---|---|---|---|---|---|---|---|---|
| | | | | k(0) | k(1) | k(2) | k(3) | 1 | 2 | 3 | | | |
| 2-Methylhexane | GC-PIANO | 1.883–4.118 | 2.852 | 73.421 | −45.227 | −180.792 | −128.404 | (1) 1804 | aromatic 1592 | methylene 1244 | 0.907 | 0.823 | 0.156 |
| 2,2-Dimethylbutane | GC-PIANO | 0.339–1.076 | 0.0721 | −19.744 | 12.635 | 85.006 | 32.918 | methylene 1828 | olefin 1332 | methylene 1162 | 0.908 | 0.825 | 0.0621 |
| 2,3-Dimethylbutane | GC-PIANO | 0.461–0.850 | 0.7 | −0.070 | −19.360 | 6.277 | −15.599 | methylene 2050 | methyl 1828 | methyl 1182 | 0.873 | 0.761 | 0.0408 |
| 2-Methylpentane | GC-PIANO | 2.625–4.290 | 3.409 | 33.716 | −34.183 | −177.647 | −53.891 | (1) 1844 | methylene 1256 | methyl 1620 | 0.844 | 0.713 | 0.191 |
| 3-Methylpentane | GC-PIANO | 1.992–3.204 | 2.595 | −4.712 | −36.378 | −62.348 | 20.188 | methylene 1186 | 2052 | aromatic 1824 | 0.846 | 0.716 | 0.137 |
| Napthenes | GC-PIANO | 0.811–6.511 | 1.772 | −17.732 | 285.844 | 648.948 | 67.139 | methyl 1368 | (1) 1294 | methylene 1802 | 0.986 | 0.972 | 0.225 |
| Methylcyclopentane | GC-PIANO | 0.165–1.875 | 0.433 | 2.228 | −53.642 | 103.606 | 46.526 | methyl 1192 | (1) 1374 | methylene 1234 | 0.977 | 0.973 | 0.058 |
| | | | | | | | | methyl | methyl | methyne:t-butyl or methylene | | | |

(1) NOT ASSIGNED

TABLE B

Comparision of NIR Results with GC-PIANO Results
For Reformates in the 1100-2500 nm Range

| | TOTAL AROMATICS | | | OLEFINS | | |
|---|---|---|---|---|---|---|
| SAMPLE | NIR | GC-PIANO | Delta | NIR | GC-PIANO | Delta |
| 4/15/94 | 67.139 | 66.997 | 0.142 | 1.366 | 1.401 | −0.035 |
| 4/16/94 | 65.361 | 64.925 | 0.436 | 1.226 | 1.416 | −0.190 |
| 4/17/94 | 65.438 | 65.392 | 0.046 | 1.221 | 1.359 | −0.138 |
| 4/23/94 | 65.799 | 65.237 | 0.562 | 1.081 | 1.337 | −0.256 |
| 4/24/94 | 65.884 | 65.760 | 0.124 | 1.102 | 1.302 | −0.200 |
| 4/25/94 | 64.867 | 64.474 | 0.393 | 1.259 | 1.435 | −0.176 |
| 4/26/94 | 65.190 | 64.902 | 0.288 | 1.254 | 1.492 | −0.238 |
| 4/27/94 | 65.026 | 65.703 | −0.677 | 1.199 | 1.393 | −0.194 |
| 4/28/94 | 65.450 | 65.602 | −0.152 | 1.238 | 1.444 | −0.206 |
| Average Deltas | | | 0.129 | | | −0.181 |
| SEP | | | 0.373 | | | 0.065 |

| | BENZENE | | | TOLUENE | | | XYLENE + ETHYLBENZENE | | |
|---|---|---|---|---|---|---|---|---|---|
| SAMPLE | NIR | GC-PIANO | Delta | NIR | GC-PIANO | Delta | NIR | GC-PIANO | Delta |
| 4/15/94 | 5.222 | 5.183 | 0.039 | 14.843 | 15.201 | −0.358 | 22.007 | 21.115 | 0.892 |
| 4/16/94 | 3.597 | 3.843 | −0.246 | 14.177 | 13.601 | 0.576 | 21.620 | 21.557 | 0.063 |
| 4/17/94 | 3.804 | 4.143 | −0.339 | 14.381 | 14.317 | 0.064 | 21.275 | 21.657 | −0.382 |
| 4/23/94 | 3.129 | 3.574 | −0.445 | 13.983 | 13.370 | 0.613 | 21.000 | 20.724 | 0.276 |
| 4/24/94 | 2.888 | 3.377 | −0.489 | 14.037 | 13.402 | 0.635 | 20.999 | 21.076 | −0.077 |
| 4/25/94 | 3.375 | 3.692 | −0.317 | 14.083 | 13.592 | 0.491 | 21.084 | 21.655 | −0.571 |
| 4/26/94 | 3.548 | 3.792 | −0.244 | 14.278 | 13.781 | 0.497 | 21.458 | 22.065 | −0.607 |
| 4/27/94 | 3.149 | 3.444 | −0.295 | 13.907 | 13.380 | 0.527 | 21.229 | 21.744 | −0.515 |
| 4/28/94 | 3.186 | 3.541 | −0.355 | 14.006 | 13.465 | 0.541 | 21.107 | 21.515 | −0.408 |
| Average Deltas | | | −0.299 | | | 0.398 | | | −0.148 |
| SEP | | | 0.161 | | | 0.330 | | | 0.495 |

TABLE C

Partial Least Squares Regression Equations for Reformate Using
Second Derivative Data in the 1100-2500 nm Range

| Compound Volume % | Primary Method | Range | Average | Wavelength Range (nm) | Factors | R | $R^2$ | NIR STD ERROR |
|---|---|---|---|---|---|---|---|---|
| Total Aromatics | GC-PIANO | 35.917–68.001 | 59.758 | 1214–1260; 1600–1670; 1780–1858 | 5 | 0.999 | 0.998 | 0.3248 |
| Benzene | GC-PIANO | 2.697–5.730 | 4.394 | 1120–1260; 1600–1670; 1780–1858; 2100–2160 | 12 | 1.000 | 0.999 | 0.0228 |
| Toluene | GC-PIANO | 8.770–16.169 | 13.633 | 1214–1230; 1600–1670; 1780–1858; 2000–2160 | 8 | 0.997 | 0.995 | 0.1294 |
| Total Xylenes | GC-PIANO | 8.512–19.999 | 15.596 | 1120–1214; 1320–1530; 1600–1670; 2000–2040 | 12 | 0.998 | 0.995 | 0.215 |
| m-Xylene | GC-PIANO | 4.013–9.572 | 7.657 | 1320–1430; 1480–1530; 1600–1670; 2000–2040 | 7 | 0.991 | 0.981 | 0.1863 |
| p-Xylene | GC-PIANO | 1.802–4.034 | 3.258 | 1156–1214; 1320–1430; 1600–1670; 2000–2040 | 12 | 0.997 | 0.995 | 0.0437 |
| o-Xylene | GC-PIANO | 2.697–6.393 | 5.063 | 1600–1670; 1780–1858; 2000–2040; 2100–2160 | 8 | 0.995 | 0.990 | 0.1098 |
| Ethyl-Benzene | GC-PIANO | 2.292–3.960 | 3.259 | 1156–1284; 1600–1670 | 5 | 0.983 | 0.967 | 0.0869 |
| n-Propylbenzene | GC-PIANO | 0.832–1.297 | 1.113 | 1156–1214; 1320–1480; 1600–1670; 1970–2040 | 8 | 0.987 | 0.973 | 0.0232 |
| Total Xylenes + Ethyl-Benzene | GC-PIANO | 10.804–23.959 | 18.855 | 1120–1214; 1600–1670; 1780–1858; 1970–2040; 2160–2250 | 13 | 0.999 | 0.998 | 0.1455 |
| BTX | GC-PIANO | 19.979–40.253 | 33.623 | 1214–1260; 1600–1670; 1760–1858; 2000–2040 | 6 | 0.997 | 0.994 | 0.377 |
| BTEX | GC-PIANO | 22.271–44.213 | 36.882 | 1156–1214; 1600–1670; 1780–1858; 1970–2040; 2100–2160 | 5 | 0.993 | 0.986 | 0.6264 |
| Olefins | GC-PIANO | 0.464–1.697 | 1.083 | 1132–1214; 1600–1670 | 6 | 0.973 | 0.947 | 0.06 |
| Paraffins | GC-PIANO | 8.355–22.359 | 11.084 | 1214–1264; 1940–2100 | 6 | 0.998 | 0.996 | 0.1923 |
| n-Pentane | GC-PIANO | 0.685–4.823 | 1.818 | 1430–1480; 1600–1670; 1940–2040 | 7 | 0.965 | 0.932 | 0.2528 |
| n-Hexane | GC-PIANO | 2.673–5.185 | 3.527 | 1430–1480; 1780–1858 | 9 | 0.961 | 0.923 | 0.1404 |
| n-Heptane | GC-PIANO | 1.612–7.484 | 2.869 | 1158–1214; 1320–1480; 1600–1670 | 8 | 0.995 | 0.989 | 0.0916 |
| Isoparaffins | GC-PIANO | 20.004–34.565 | 24.081 | 1214–1264; 1920–2100 | 7 | 0.998 | 0.995 | 0.2708 |
| Iso-Pentane | GC-PIANO | 1.058–8.247 | 2.937 | 1430–1500; 1940–2040; 2100–2160 | 13 | 0.994 | 0.988 | 0.1914 |
| 2-Methylhexane | GC-PIANO | 1.883–4.118 | 2.852 | 1214–1260; 1560–1626; 1780–1858 | 11 | 0.974 | 0.949 | 0.0916 |
| 2,2-Dimethylbutane | GC-PIANO | 0.339–1.076 | 0.721 | 1156–1214; 1320–1430; 1780–1858 | 5 | 0.923 | 0.852 | 0.0582 |
| 2,3-Dimethylbutane | GC-PIANO | 0.461–0.850 | 0.7 | 1156–1214; 1780–1858; 2000–2160 | 8 | 0.957 | 0.915 | 0.0256 |
| 2-Methylpentane | GC-PIANO | 2.625–4.290 | 3.409 | 1230–1264; 1600–1670; 1780–1858; 1900–2000 | 9 | 0.919 | 0.844 | 0.151 |
| 3-Methylpentane | GC-PIANO | 1.992–3.204 | 2.595 | 1156–1214; 1780–1858; 2000–2160 | 8 | 0.948 | 0.899 | 0.0866 |
| Naphthenes | GC-PIANO | 0.811–6.511 | 1.772 | 1264–1430; 1780–1858 | 12 | 0.998 | 0.997 | 0.0849 |
| Methylcyclopentane | GC-PIANO | 0.165–1.875 | 0.433 | 1156–1260; 1320–1430 | 4 | 0.988 | 0.975 | 0.0564 |

TABLE D

Multiple Linear Regression Equations for Gasoline Using Second Derivative Data in the 800–1100 nm Range

| Compound Volume % | Primary Method | Range | Average | k(0) | k(1) | k(2) | k(3) |
|---|---|---|---|---|---|---|---|
| Total Aromatics | GC-PIANO | 15.807–53.948 | 27.184 | −5.997 | 849.956 | 2093.227 | −941.626 |
| Benzene | GC-PIANO | 0.209–3.464 | 1.021 | 5.957 | −223.324 | 14.679 | −282.507 |
| Toluene | GC-PIANO | 1.103–16.177 | 4.418 | −48.597 | 875.582 | 577.698 | 1586.754 |
| Total Xylenes | GC-PIANO | 3.869–17.130 | 6.685 | −10.873 | 118.346 | 414.531 | 2652.921 |
| m-Xylene | GC-PIANO | 1.942–9.108 | 3.250 | −15.071 | 148.824 | 618.061 | 849.797 |
| p-Xylene | GC-PIANO | 0.742–3.773 | 1.333 | −0.891 | 331.087 | 47.028 | −218.152 |
| o-Xylene | GC-PIANO | 1.133–4.728 | 2.102 | 1.238 | −66.080 | −98.546 | −174.507 |
| Ethyl-Benzene | GC-PIANO | 0.444–4.110 | 1.193 | −0.229 | −316.535 | −474.194 | 343.881 |

| Compound Volume % | Wavelengths (nm) 1 | 2 | 3 | R | $R^2$ | NIR STD ERROR |
|---|---|---|---|---|---|---|
| Total Aromatics | 1064 | 854 | 879.5 | 0.983 | 0.966 | 1.35 |
| Benzene | 886 | 914.5 | 871 | 0.894 | 0.799 | 0.208 |
| Toluene | 884.5 | 892.5 | 989.5 | 0.907 | 0.823 | 0.909 |
| Total Xylenes | 920 | 879 | 868 | 0.882 | 0.777 | 0.955 |
| m-Xylene | 906 | 973 | 868 | 0.803 | 0.644 | 0.599 |
| p-Xylene | 867.5 | 906.5 | 857.5 | 0.785 | 0.616 | 0.265 |
| o-Xylene | 954.5 | 880.5 | 964.5 | 0.967 | 0.935 | 0.186 |
| Ethyl-Benzene | 1028 | 861 | 887.5 | 0.664 | 0.441 | 0.329 |

TABLE E

Partial Least Squares Regression Equations for Gasoline Using Second Derivative Data in the 800–1100 nm Range

| Compound Volume % | Primary Method | Range | Average | Wavelength Range (nm) | Factors | R | $R^2$ | NIR STD ERROR |
|---|---|---|---|---|---|---|---|---|
| Total Aromatics | GC-PIANO | 15.807–53.948 | 27.184 | 840–900; 1050–1075 | 3 | 0.985 | 0.969 | 1.2455 |
| Benzene | GC-PIANO | 0.209–3.464 | 1.021 | 850–925 | 9 | 0.935 | 0.874 | 0.1723 |
| Toluene | GC-PIANO | 1.103–16.177 | 4.418 | 860–910; 975–1000 | 6 | 0.918 | 0.842 | 0.749 |
| Total Xylenes | GC-PIANO | 3.869–17.130 | 6.685 | 850–930 | 9 | 0.923 | 0.852 | 0.8112 |
| m-Xylene | GC-PIANO | 1.942–9.108 | 3.250 | 850–925; 965–990 | 7 | 0.864 | 0.747 | 0.5271 |
| p-Xylene | GC-PIANO | 0.742–3.773 | 1.333 | 850–925 | 10 | 0.881 | 0.776 | 0.2141 |
| o-Xylene | GC-PIANO | 1.133–4.728 | 2.102 | 865–900; 940–975 | 8 | 0.975 | 0.950 | 0.1652 |
| Ethyl-Benzene | GC-PIANO | 0.444–4.110 | 1.193 | 850–900; 1015–1045 | 9 | 0.844 | 0.712 | 0.2494 |

TABLE F

Comparison Between GC-PIANO Results and NIR Results for Gasolines in the 800–1100 nm Range Using PLSR

| SAMPLE | TOTAL AROMATICS | | | BENZENE | | | TOLUENE | | | TOTAL XYLENES | | |
|---|---|---|---|---|---|---|---|---|---|---|---|---|
| | NIR | GC-PIANO | Δ | NIR | GC-PIANO | Δ | NIR | GC-PIANO | Δ | NIR | GC-PIANO | Δ |
| cat-15 | 46.261 | 45.742 | 0.519 | 0.720 | 0.611 | 0.109 | 1.757 | 2.961 | −1.204 | 11.067 | 10.460 | 0.607 |
| cat-26 | 16.234 | 16.615 | −0.381 | 0.854 | 0.649 | 0.235 | 2.328 | 3.397 | −1.069 | 4.412 | 4.004 | 0.408 |
| cat-42 | 21.188 | 21.476 | −0.288 | 1.039 | 0.828 | 0.211 | 3.506 | 3.929 | −0.423 | 5.764 | 5.372 | 0.392 |
| cat-86 | 24.050 | 25.780 | −1.730 | 0.761 | 0.850 | −0.099 | 3.756 | 4.966 | −1.210 | 5.835 | 5.930 | −0.095 |
| cat-99 | 24.174 | 22.954 | 1.220 | 0.891 | 1.010 | −0.119 | 4.797 | 2.515 | 2.282 | 2.843 | 6.248 | −3.405 |
| cat-118 | 26.510 | 29.440 | −0.930 | 1.031 | 0.937 | 0.994 | 3.625 | 4.258 | −0.633 | 7.192 | 7.040 | 0.152 |
| cat-139 | 26.936 | 27.984 | −1.048 | 0.904 | 0.615 | 0.289 | 7.695 | 10.200 | −2.565 | 6.340 | 5.078 | 1.262 |
| cat-150 | 28.539 | 27.664 | 0.875 | 2.254 | 1.982 | 0.272 | 8.107 | 7.508 | 0.599 | 8.102 | 7.546 | 0.556 |
| cat-163 | 20.481 | 19.927 | 0.554 | 0.761 | 1.113 | −0.352 | 5.387 | 3.877 | 1.510 | 4.919 | 6.103 | −1.184 |
| AVERAGES | | | −0.134 | | | 0.068 | | | −0.295 | | | −0.145 |
| Std Error of Pred. | | | 1.100 | | | 0.175 | | | 1.350 | | | 1.300 |

| SAMPLE | m-XYLENE | | | p-XYLENE | | | o-XYLENE | | | ETHYLBENZENE | | |
|---|---|---|---|---|---|---|---|---|---|---|---|---|
| | NIR | GC-PIANO | Δ | NIR | GC-PIANO | Δ | NIR | GC-PIANO | Δ | NIR | GC-PIANO | Δ |
| cat-15 | 5.027 | 4.450 | 0.577 | 1.846 | 1.762 | 0.084 | 4.119 | 4.248 | −0.129 | 1.613 | 1.377 | 0.236 |
| cat-26 | 2.345 | 2.041 | 0.304 | 0.930 | 0.825 | 0.105 | 1.008 | 1.138 | −0.130 | 0.914 | 0.847 | 0.067 |

TABLE F-continued

Comparison Between GC-PIANO Results and NIR Results for Gasolines in the 800–1100 nm Range Using PLSR

| | | | | | | | | | | | | |
|---|---|---|---|---|---|---|---|---|---|---|---|---|
| cat-42 | 2.837 | 2.718 | 0.119 | 1.206 | 1.099 | 0.107 | 1.587 | 1.555 | 0.032 | 1.406 | 1.034 | 0.372 |
| cat-86 | 2.771 | 2.918 | −0.147 | 1.109 | 1.211 | −0.102 | 1.696 | 1.801 | −0.105 | 0.975 | 1.098 | −0.123 |
| cat-99 | 1.588 | 3.106 | −1.518 | 1.178 | 1.288 | −0.110 | 2.118 | 1.854 | 0.264 | 0.381 | 1.191 | −0.810 |
| cat-118 | 3.621 | 3.369 | 0.232 | 1.448 | 1.371 | 0.077 | 2.246 | 2.280 | −0.034 | 1.243 | 1.226 | 0.017 |
| cat-139 | 3.661 | 2.409 | 1.252 | 1.409 | 0.955 | 0.454 | 1.969 | 1.714 | 0.255 | 1.189 | 0.789 | 0.400 |
| cat-150 | 2.997 | 3.911 | −0.914 | 1.622 | 1.664 | −0.042 | 2.155 | 1.971 | 0.184 | 1.596 | 1.722 | −0.126 |
| cat-163 | 1.797 | 3.097 | −1.300 | 0.765 | 1.378 | −0.613 | 1.324 | 1.628 | −0.304 | 1.253 | 1.427 | −0.174 |
| | | | −0.155 | | | −0.004 | | | 0.004 | | | −0.016 |
| | | | 0.849 | | | 0.188 | | | 0.112 | | | 0.414 |

TABLE G

GC-PIANO Results Listing Selected Speciations

| SAMPLE # | Aromatics | Olefins | Benzene | Toluene | Xylenes | m-Xylene | p-Xylene | o-Xylene | Ethyl-benzene | n-Propyl-benzene | Paraffins | Pentane | Hexane | n-heptane | Iso-Paraffins | Iso-Pentane | 2-Methyl-hexane | Naph-thenes | Methyl-cyclopentane |
|---|---|---|---|---|---|---|---|---|---|---|---|---|---|---|---|---|---|---|---|
| LPCCR-33 | 35.917 | 0.464 | 2.697 | 8.770 | 8.512 | 4.013 | 1.802 | 2.697 | 2.292 | 0.858 | 22.189 | 0.685 | 5.185 | 7.484 | 34.195 | 1.058 | 4.118 | 6.511 | 1.489 |
| LPCCR-28 | 50.071 | 1.072 | 3.476 | 11.730 | 12.518 | 5.885 | 2.615 | 4.018 | 2.803 | 0.969 | 15.436 | 4.823 | 4.076 | 3.546 | 30.457 | 8.247 | 2.820 | 2.090 | 0.618 |
| LPCCR-30 | 56.081 | 1.172 | 3.613 | 12.847 | 14.286 | 6.725 | 2.954 | 4.607 | 3.080 | 1.043 | 12.231 | 4.162 | 3.702 | 2.953 | 26.915 | 7.968 | 2.487 | 1.495 | 0.470 |
| LPCCR-31 | 57.164 | 1.221 | 3.665 | 13.048 | 14.610 | 6.880 | 3.008 | 4.722 | 3.119 | 1.050 | 12.899 | 4.187 | 3.649 | 2.800 | 26.202 | 7.921 | 2.429 | 1.352 | 0.434 |
| LPCCR-33 | 59.055 | 1.042 | 3.779 | 12.930 | 14.944 | 7.232 | 3.091 | 4.621 | 3.058 | 1.040 | 13.730 | 2.320 | 2.982 | 2.519 | 23.973 | 3.627 | 2.677 | 0.912 | 0.165 |
| LPCCR-34 | 58.841 | 1.067 | 3.830 | 12.799 | 14.834 | 7.196 | 3.056 | 4.582 | 3.043 | 1.037 | 12.790 | 2.282 | 3.167 | 2.648 | 24.957 | 3.621 | 2.809 | 1.009 | 0.190 |
| LPCCR-35 | 61.540 | 1.016 | 3.993 | 13.379 | 15.441 | 7.492 | 3.212 | 4.737 | 3.191 | 1.091 | 10.697 | 2.158 | 3.310 | 2.835 | 24.323 | 3.290 | 2.997 | 1.127 | 0.024 |
| LPCCR-45 | 43.377 | 0.511 | 3.962 | 11.292 | 10.319 | 5.308 | 2.265 | 2.746 | 2.372 | 1.091 | 14.768 | 2.329 | 4.504 | 3.923 | 34.565 | 3.604 | 3.639 | 6.029 | 1.875 |
| LPCCR-47 | 49.901 | 0.669 | 4.786 | 12.891 | 12.041 | 6.171 | 2.662 | 3.208 | 2.682 | 0.832 | 13.626 | 3.040 | 4.271 | 3.123 | 31.137 | 4.284 | 3.180 | 3.915 | 1.189 |
| LPCCR-48 | 52.750 | 0.796 | 5.131 | 13.542 | 12.835 | 6.600 | 2.814 | 3.421 | 2.786 | 0.893 | 14.512 | 3.244 | 4.009 | 2.597 | 28.642 | 4.771 | 2.772 | 2.748 | 0.846 |
| LPCCR-50 | 60.571 | 1.064 | 5.730 | 15.490 | 15.419 | 7.921 | 3.378 | 4.120 | 3.168 | 0.890 | 13.373 | 3.509 | 3.522 | 1.660 | 22.731 | 4.812 | 1.941 | 1.334 | 0.383 |
| LPCCR-51 | 59.801 | 1.099 | 5.498 | 15.112 | 15.256 | 7.828 | 3.334 | 4.094 | 3.124 | 0.896 | 14.670 | 3.245 | 3.379 | 1.612 | 22.330 | 4.383 | 1.883 | 1.157 | 0.364 |
| LPCCR-59 | 52.818 | 1.440 | 3.647 | 12.395 | 13.335 | 6.669 | 2.851 | 3.815 | 2.872 | 0.946 | 13.962 | 2.309 | 3.606 | 3.362 | 27.254 | 3.052 | 2.895 | 3.579 | 0.769 |
| LPCCR-64 | 51.648 | 1.599 | 3.724 | 12.086 | 12.932 | 6.453 | 2.767 | 3.712 | 2.825 | 0.937 | 14.141 | 2.247 | 3.984 | 3.622 | 27.237 | 2.913 | 2.917 | 4.377 | 0.952 |
| LPCCR-70 | 49.160 | 1.697 | 3.595 | 11.395 | 12.258 | 6.092 | 2.617 | 3.549 | 2.735 | 0.916 | 15.102 | 2.067 | 4.212 | 3.849 | 28.330 | 2.652 | 2.949 | 4.654 | 1.023 |
| LPCCR-72 | 50.948 | 1.293 | 3.852 | 12.799 | 12.388 | 6.134 | 2.634 | 3.620 | 2.706 | 0.971 | 14.720 | 2.011 | 4.167 | 3.581 | 27.692 | 2.697 | 2.860 | 4.205 | 0.951 |
| LPCCR-77 | 58.810 | 1.053 | 4.394 | 12.622 | 13.856 | 6.708 | 2.856 | 4.292 | 2.797 | 1.140 | 11.836 | 2.148 | 3.590 | 2.538 | 24.587 | 3.154 | 2.452 | 1.994 | 0.402 |
| LPCCR-78 | 58.990 | 1.049 | 4.432 | 12.680 | 13.890 | 6.739 | 2.845 | 4.306 | 2.802 | 1.143 | 11.769 | 2.158 | 3.600 | 2.537 | 24.476 | 3.172 | 2.451 | 2.000 | 0.402 |
| LPCCR-79 | 58.646 | 0.871 | 4.745 | 12.438 | 13.355 | 6.328 | 2.651 | 4.376 | 2.962 | 1.193 | 11.750 | 1.573 | 3.768 | 2.982 | 25.585 | 2.516 | 2.979 | 1.626 | 0.357 |
| LPCCR-80 | 60.431 | 0.904 | 4.898 | 12.799 | 14.276 | 6.714 | 2.858 | 4.704 | 3.057 | 1.192 | 10.755 | 1.513 | 3.651 | 2.802 | 25.202 | 2.493 | 2.837 | 1.398 | 0.301 |
| LPCCR-81 | 62.726 | 0.841 | 5.012 | 13.154 | 14.458 | 6.843 | 2.848 | 4.767 | 3.172 | 1.256 | 10.335 | 1.491 | 3.542 | 2.715 | 23.079 | 2.435 | 2.770 | 1.359 | 0.310 |
| LPCCR-82 | 60.374 | 0.812 | 4.954 | 12.631 | 13.676 | 6.470 | 2.719 | 4.467 | 3.062 | 1.239 | 10.576 | 1.140 | 3.821 | 3.060 | 24.993 | 1.984 | 3.010 | 1.702 | 0.415 |
| LPCCR-83 | 59.175 | 0.786 | 4.879 | 12.483 | 13.253 | 6.281 | 2.634 | 4.338 | 3.019 | 1.235 | 10.622 | 1.043 | 3.858 | 3.340 | 25.721 | 1.847 | 3.158 | 1.959 | 0.486 |
| LPCCR-84 | 56.288 | 0.818 | 4.691 | 12.239 | 13.073 | 6.199 | 2.590 | 4.284 | 2.990 | 1.210 | 11.093 | 1.056 | 4.163 | 3.341 | 26.241 | 1.912 | 3.153 | 1.987 | 0.491 |
| LPCCR-85 | 51.177 | 0.917 | 3.612 | 12.151 | 14.591 | 6.917 | 2.973 | 4.701 | 2.957 | 1.108 | 11.849 | 1.374 | 3.776 | 3.408 | 27.353 | 2.697 | 3.314 | 1.666 | 0.385 |
| LPCCR-86 | 63.796 | 1.332 | 4.380 | 14.063 | 16.487 | 7.857 | 3.392 | 5.238 | 3.593 | 1.288 | 9.559 | 1.141 | 3.266 | 2.852 | 21.861 | 1.922 | 2.511 | 1.575 | 0.387 |
| LPCCR-87 | 63.752 | 1.236 | 4.585 | 14.553 | 16.500 | 7.846 | 3.367 | 5.287 | 3.591 | 1.257 | 9.457 | 1.034 | 3.412 | 2.989 | 22.271 | 1.611 | 3.020 | 1.533 | 0.396 |
| LPCCR-88 | 64.043 | 1.187 | 4.691 | 14.461 | 16.817 | 7.973 | 3.410 | 5.434 | 3.547 | 1.233 | 9.399 | 1.171 | 3.483 | 2.807 | 22.501 | 2.081 | 2.987 | 1.179 | 0.297 |
| LPCCR-89 | 65.640 | 1.128 | 4.540 | 14.431 | 17.209 | 8.154 | 3.454 | 5.601 | 3.639 | 1.269 | 8.821 | 1.007 | 3.358 | 2.870 | 21.922 | 1.718 | 3.027 | 1.332 | 0.288 |
| LPCCR-90 | 63.792 | 1.109 | 4.252 | 13.579 | 16.897 | 7.924 | 3.426 | 5.547 | 3.603 | 1.241 | 9.240 | 1.185 | 3.550 | 2.998 | 23.589 | 2.134 | 3.200 | 1.325 | 0.276 |
| LPCCR-91 | 67.888 | 1.293 | 4.255 | 15.244 | 19.049 | 9.091 | 3.844 | 6.114 | 3.783 | 1.185 | 8.938 | 1.529 | 3.172 | 2.189 | 20.316 | 2.451 | 2.472 | 0.811 | 0.196 |
| LPCCR-92 | 67.639 | 1.333 | 4.194 | 14.973 | 18.918 | 8.992 | 3.834 | 6.092 | 3.785 | 1.202 | 8.697 | 1.412 | 3.255 | 2.330 | 20.505 | 2.297 | 2.582 | 1.004 | 0.221 |
| LPCCR-93 | 67.176 | 1.277 | 4.455 | 15.515 | 18.764 | 8.903 | 3.797 | 6.064 | 3.715 | 1.168 | 8.925 | 1.330 | 3.240 | 2.465 | 20.758 | 2.222 | 2.712 | 1.065 | 0.242 |
| LPCCR-94 | 67.961 | 1.304 | 4.620 | 15.679 | 19.210 | 9.150 | 3.878 | 6.162 | 3.737 | 1.160 | 8.504 | 1.392 | 3.337 | 2.344 | 20.566 | 2.320 | 2.620 | 0.955 | 0.227 |
| LPCCR-95 | 66.013 | 1.335 | 4.512 | 14.982 | 18.352 | 8.739 | 3.688 | 5.925 | 3.568 | 1.144 | 9.502 | 1.393 | 3.553 | 2.356 | 21.375 | 2.338 | 2.627 | 0.946 | 0.240 |
| LPCCR-96 | 66.666 | 1.348 | 4.143 | 14.625 | 18.698 | 8.716 | 3.734 | 5.927 | 3.734 | 1.182 | 9.047 | 1.445 | 3.827 | 2.345 | 21.847 | 2.355 | 2.601 | 1.128 | 0.255 |
| LPCCR-97 | 66.090 | 1.412 | 4.202 | 14.223 | 18.377 | 8.857 | 3.768 | 6.075 | 3.685 | 1.166 | 9.239 | 1.436 | 3.384 | 2.322 | 21.050 | 2.369 | 2.601 | 0.972 | 0.211 |
| LPCCR-98 | 67.334 | 1.361 | 4.341 | 15.148 | 18.733 | 8.936 | 3.776 | 6.021 | 3.689 | 1.158 | 9.155 | 1.497 | 3.391 | 2.210 | 20.592 | 2.433 | 2.480 | 0.891 | 0.219 |
| LPCCR-99 | 66.545 | 1.181 | 4.983 | 16.169 | 18.582 | 8.989 | 3.796 | 5.795 | 3.640 | 1.078 | 8.546 | 1.885 | 3.621 | 2.401 | 22.158 | 2.958 | 2.671 | 1.036 | 0.229 |
| LPCCR-100 | 55.855 | 0.968 | 4.131 | 12.886 | 15.009 | 7.420 | 3.198 | 4.391 | 3.143 | 0.952 | 12.904 | 2.273 | 3.348 | 3.165 | 28.138 | 3.464 | 3.489 | 1.639 | 0.369 |
| LPCCR-101 | 68.001 | 0.847 | 5.388 | 15.379 | 17.104 | 8.164 | 3.411 | 5.529 | 3.584 | 1.297 | 8.897 | 1.084 | 2.984 | 2.441 | 20.004 | 1.909 | 2.656 | 1.054 | 0.263 |
| LPCCR-102 | 67.702 | 0.930 | 5.410 | 15.863 | 17.542 | 8.164 | 3.453 | 5.668 | 3.635 | 1.284 | 8.414 | 1.156 | 2.673 | 2.607 | 20.938 | 2.060 | 2.867 | 1.059 | 0.249 |
| LPCCR-103 | 67.961 | 0.935 | 5.674 | 15.462 | 16.978 | 8.063 | 3.364 | 5.551 | 3.733 | 1.295 | 8.922 | 1.062 | 3.250 | 2.786 | 21.557 | 1.965 | 2.987 | 1.236 | 0.318 |
| LPCCR-104 | 66.759 | 1.150 | 5.408 | 15.771 | 18.065 | 8.639 | 3.610 | 5.816 | 3.744 | 1.190 | 8.688 | 1.290 | 3.248 | 2.661 | 21.580 | 2.268 | 2.927 | 1.087 | 0.283 |
| LPCCR-105 | 67.253 | 1.181 | 5.411 | 15.946 | 18.275 | 8.736 | 3.686 | 5.853 | 3.778 | 1.191 | 8.846 | 1.310 | 3.153 | 2.560 | 21.105 | 2.267 | 2.825 | 0.897 | 0.257 |
| LPCCR-106 | 66.863 | 1.189 | 4.996 | 15.232 | 18.615 | 8.332 | 3.782 | 6.001 | 3.855 | 1.207 | 8.716 | 1.344 | 3.284 | 2.610 | 21.527 | 2.331 | 2.885 | 1.067 | 0.252 |

TABLE G-continued

GC-PIANO Results Listing Selected Speciations

| SAMPLE # | Aromatics | Olefins | Benzene | Toluene | Xylenes | m-Xylene | p-Xylene | o-Xylene | Ethyl-benzene | n-Propyl-benzene | Paraffins | Pentane | Hexane | n-heptane | Iso-Paraffins | Iso-Pentane | 2-Methyl-hexane | Naphthenes | Methyl-cyclopentane |
|---|---|---|---|---|---|---|---|---|---|---|---|---|---|---|---|---|---|---|---|
| LPCCR-107 | 67.643 | 1.174 | 4.674 | 15.767 | 19.324 | 9.237 | 3.888 | 6.199 | 3.901 | 1.170 | 8.555 | 1.333 | 2.961 | 2.651 | 20.916 | 2.281 | 2.915 | 1.044 | 0.229 |
| LPCCR-108 | 66.200 | 1.249 | 4.647 | 15.532 | 19.434 | 8.271 | 3.937 | 6.226 | 3.894 | 1.095 | 9.015 | 1.371 | 3.244 | 2.673 | 21.811 | 2.364 | 2.954 | 1.029 | 0.236 |
| LPCCR-109 | 66.528 | 1.203 | 4.461 | 15.524 | 19.511 | 9.288 | 3.963 | 6.250 | 3.912 | 1.112 | 9.148 | 1.300 | 2.987 | 2.716 | 21.331 | 2.244 | 2.974 | 1.064 | 0.233 |
| LPCCR-110 | 66.739 | 1.230 | 4.672 | 15.680 | 19.553 | 9.319 | 3.974 | 6.260 | 3.896 | 1.117 | 8.803 | 1.389 | 3.126 | 2.671 | 21.612 | 2.415 | 2.970 | 1.024 | 0.232 |
| LPCCR-111 | 66.913 | 1.147 | 4.452 | 15.802 | 19.999 | 9.572 | 4.034 | 6.393 | 3.960 | 1.130 | 9.029 | 1.369 | 2.807 | 2.706 | 21.386 | 2.397 | 2.997 | 1.008 | 0.214 |
| LPCCR-112 | 67.335 | 1.201 | 4.536 | 15.704 | 19.507 | 9.290 | 3.932 | 6.285 | 3.835 | 1.156 | 8.976 | 1.290 | 3.011 | 2.602 | 20.988 | 2.239 | 2.868 | 0.981 | 0.222 |

TABLE H

P.I.A.N.O. ANALYSIS
by Analytical Automation Specialists, Inc.
Licensed to: Ashland Petroleum Co. - Catlettsburg, KY

| | | | |
|---|---|---|---|
| | Sample: LPCCR 79 | Acquired on: 01-07-1994 | |
| | File: K168.ATB | Normalized to 100% | |
| | RI Data File: PRODUCT | Processed 253 Peaks | |
| Gas Chromatograph: | Hewlett Packard 5890 | | |
| Inj. Temp | 220° C. | Sample Size | 0.2 ul |
| Det. Temp | 258° C. | Split Ratio | 131.8 |
| Carrier Gas: | Helium | Carrier Pressure | 38 psi |
| Column: | Supelco DH-100 100M | Installed on | |
| Conditions: | 35 deg C. | | |
| Rate 2: | Methane set to 7.00 min. | | |

Composite Report
Hydrocarbon Totals by Group Type

| Type | Wt % | Vol % | Mol % |
|---|---|---|---|
| Total Paraffins: | 9.722 | 11.750 | 11.615 |
| Total Iso-paraffins: | 21.692 | 25.585 | 23.531 |
| Total Naphthenes: | 1.554 | 1.626 | 1.624 |
| Total Aromatics: | 64.681 | 58.646 | 61.389 |
| Total Olefins: | 0.763 | 0.871 | 0.878 |
| Total C14+ | 0.492 | 0.511 | 0.252 |
| Total Unknowns: | 1.097 | 1.012 | 0.711 |
| Total: | 100.000 | 100.000 | 100.000 |

Totals by Carbon Number

| Group | Wt % | Vol % | Mol % | Ave. Mw. | Ave. Sp Gr. |
|---|---|---|---|---|---|
| Methane | 0.000 | 0.000 | 0.000 | 0.000 | 0.000 |
| Ethane | 0.000 | 0.000 | 0.000 | 0.000 | 0.000 |
| Propane | 0.008 | 0.012 | 0.018 | 44.097 | 0.501 |
| Butanes: | 1.849 | 2.555 | 3.235 | 58.097 | 0.573 |
| Pentanes: | 3.500 | 4.407 | 4.943 | 71.978 | 0.629 |
| Hexanes: | 15.490 | 16.987 | 18.927 | 83.186 | 0.722 |
| Heptanes: | 24.982 | 25.553 | 26.558 | 95.610 | 0.774 |
| Octanes: | 23.118 | 22.128 | 21.787 | 107.849 | 0.827 |
| Nonanes: | 17.900 | 16.431 | 15.086 | 120.598 | 0.863 |
| Decanes: | 8.429 | 7.598 | 6.393 | 134.016 | 0.879 |
| C11's: | 2.266 | 1.963 | 1.570 | 146.715 | 0.914 |
| C12's: | 0.868 | 0.843 | 0.521 | 169.345 | 0.815 |
| C13's: | 0.000 | 0.000 | 0.000 | 0.000 | 0.000 |
| C14+ | 0.492 | 0.511 | 0.252 | | |
| Unknowns: | 1.097 | 1.012 | 0.711 | | |
| Total: | 100.000 | 100.000 | 100.000 | 102.979 | 0.779 |

Types by Carbon Number

| | | Wt % | Vol % | Mol % |
|---|---|---|---|---|
| Paraffins: | C1 | 0.000 | 0.000 | 0.000 |
| | C2 | 0.000 | 0.000 | 0.000 |
| | C3 | 0.008 | 0.012 | 0.018 |
| | C4 | 1.344 | 1.839 | 2.350 |
| | C5 | 1.244 | 1.573 | 1.752 |
| | C6 | 3.137 | 3.768 | 3.700 |
| | C7 | 2.575 | 2.982 | 2.611 |
| | C8 | 0.973 | 1.097 | 0.866 |
| | C9 | 0.253 | 0.279 | 0.201 |
| | C10 | 0.044 | 0.047 | 0.031 |
| | C11 | 0.000 | 0.000 | 0.000 |
| | C12 | 0.145 | 0.152 | 0.086 |
| | C13 | 0.000 | 0.000 | 0.000 |
| Iso-paraffins: | C4 | 0.481 | 0.684 | 0.842 |
| | C5 | 1.971 | 2.519 | 2.776 |
| | C6 | 6.519 | 7.853 | 7.688 |
| | C7 | 8.179 | 9.460 | 8.293 |
| | C8 | 3.508 | 3.940 | 3.123 |
| | C9 | 0.902 | 0.987 | 0.721 |
| | C10 | 0.074 | 0.080 | 0.053 |
| | C11 | 0.000 | 0.000 | 0.000 |
| | C12 | 0.058 | 0.061 | 0.035 |
| | C13 | 0.000 | 0.000 | 0.000 |

TABLE H-continued

P.I.A.N.O. ANALYSIS
by Analytical Automation Specialists, Inc.
Licensed to: Ashland Petroleum Co. - Catlettsburg, KY

| | | | | |
|---|---|---|---|---|
| Aromatics: | C6 | 5.266 | 4.745 | 6.852 |
| | C7 | 13.616 | 12.438 | 15.020 |
| | C8 | 17.893 | 16.316 | 17.130 |
| | C9 | 16.737 | 15.157 | 14.158 |
| | C10 | 8.273 | 7.433 | 6.281 |
| | C11 | 2.266 | 1.963 | 1.570 |
| | C12 | 0.629 | 0.594 | 0.378 |
| | C13 | 0.000 | 0.000 | 0.000 |
| Naphthenes: | C5 | 0.200 | 0.213 | 0.290 |
| | C6 | 0.356 | 0.376 | 0.430 |
| | C7 | 0.187 | 0.197 | 0.193 |
| | C8 | 0.728 | 0.758 | 0.654 |
| | C9 | 0.008 | 0.008 | 0.006 |
| | C10 | 0.039 | 0.038 | 0.028 |
| | C11 | 0.000 | 0.000 | 0.000 |
| | C12 | 0.036 | 0.036 | 0.022 |
| | C13 | 0.000 | 0.000 | 0.000 |
| Olefins: | C2 | 0.000 | 0.000 | 0.000 |
| | C3 | 0.000 | 0.000 | 0.000 |
| | C4 | 0.024 | 0.032 | 0.044 |
| | C5 | 0.085 | 0.102 | 0.124 |
| | C6 | 0.212 | 0.244 | 0.256 |
| | C7 | 0.425 | 0.476 | 0.440 |
| | C8 | 0.016 | 0.017 | 0.014 |
| | C9 | | | |
| | C12 | 0.000 | 0.000 | 0.000 |
| | C13 | 0.000 | 0.000 | 0.000 |

Components Listed in Chromatographic Order

| pk# | Min. | Index | Component | Area | Wt % | Vol % | Mol % | Grp. | Shift |
|---|---|---|---|---|---|---|---|---|---|
| 1 | 7.25 | 300.0 | Propane | 737 | 0.008 | 0.012 | 0.018 | P3 | 0.00 |
| 2 | 7.66 | 365.8 | i-Butane | 46268 | 0.481 | 0.684 | 0.842 | I4 | 0.12 |
| 3 | 7.89 | 389.7 | Butene-1/Isobutylene | 1413 | 0.014 | 0.019 | 0.026 | O4 | 1.48 |
| 4 | 8.01 | 400.0 | n-Butane | 129163 | 1.344 | 1.839 | 2.350 | P4 | 0.00 |
| 5 | 8.14 | 410.4 | t-Butene-2 | 626 | 0.006 | 0.008 | 0.011 | O4 | 0.05 |
| 6 | 8.19 | 414.4 | 2,2-Dimethylpropane | 212 | 0.002 | 0.003 | 0.003 | I5 | 0.69 |
| 7 | 8.34 | 424.8 | c-Butene-2 | 388 | 0.004 | 0.005 | 0.007 | O4 | 0.89 |
| 8 | 8.91 | 457.1 | 3-Methylbutene-1 | 238 | 0.002 | 0.003 | 0.003 | O5 | 0.92 |
| 9 | 9.31 | 474.9 | i-Pentane | 190540 | 1.969 | 2.516 | 2.773 | I5 | 0.02 |
| 10 | 9.67 | 488.8 | Pentene-1 | 342 | 0.003 | 0.004 | 0.005 | O5 | 0.12 |
| 11 | 9.87 | 495.5 | 2-Methylbutene-1 | 1671 | 0.017 | 0.020 | 0.024 | O5 | 0.05 |
| 12 | 10.01 | 500.0 | n-Pentane | 120395 | 1.244 | 1.573 | 1.752 | P5 | 0.00 |
| 13 | 10.24 | 507.6 | t-Pentene-2 | 1110 | 0.011 | 0.014 | 0.016 | O5 | 0.37 |
| 14 | 10.51 | 515.6 | c-Pentene-2 | 683 | 0.007 | 0.008 | 0.010 | O5 | 0.50 |
| 15 | 10.68 | 520.5 | 2-Methylbutene-2 | 3868 | 0.039 | 0.046 | 0.056 | O5 | 0.68 |
| 16 | 11.33 | 537.1 | 2,2-Dimethylbutane | 66357 | 0.682 | 0.832 | 0.805 | I6 | 0.22 |
| 17 | 12.15 | 554.9 | Cyclopentene | 587 | 0.006 | 0.006 | 0.009 | O5 | 0.36 |
| 18 | 12.31 | 558.1 | 4-Methylpentene-1 | 489 | 0.005 | 0.006 | 0.006 | O6 | 0.30 |
| 19 | 12.39 | 559.8 | 3-Methylpentene-1 | 691 | 0.007 | 0.008 | 0.008 | O6 | 0.23 |
| 20 | 12.73 | 566.1 | Cyclopentane/MTBE | 19965 | 0.200 | 0.213 | 0.290 | N5 | 0.29 |
| 21 | 12.81 | 567.5 | 2,3-Dimethylbutane | 58898 | 0.605 | 0.725 | 0.714 | I6 | 0.27 |
| 22 | 12.93 | 569.6 | 2,3-Dimethylbutene-1 | 470 | 0.005 | 0.006 | 0.006 | O6 | 0.26 |
| 23 | 13.05 | 571.6 | 2-Methylpentane | 285897 | 2.939 | 3.564 | 3.466 | I6 | 0.20 |
| 24 | 13.89 | 585.2 | 3-Methylpentane | 222965 | 2.292 | 2.733 | 2.703 | I6 | 0.30 |
| 25 | 14.17 | 589.2 | 2-Methylpentene-1 | 2847 | 0.029 | 0.033 | 0.034 | O6 | 0.54 |
| 26 | 14.23 | 590.1 | Hexene-1 | 821 | 0.008 | 0.010 | 0.010 | O6 | 0.29 |
| 27 | 14.95 | 600.0 | n-Hexane | 305189 | 3.137 | 3.768 | 3.700 | P6 | 0.00 |
| 28 | 15.07 | 601.8 | t-Hexene-3 | 1571 | 0.016 | 0.018 | 0.019 | O6 | 0.11 |
| 29 | 15.15 | 603.0 | c-Hexene-3 | 578 | 0.006 | 0.007 | 0.007 | O6 | 0.32 |
| 30 | 15.25 | 604.5 | t-Hexene-2 | 3141 | 0.032 | 0.037 | 0.038 | O6 | 0.24 |
| 31 | 15.41 | 606.8 | 2-Methylpentene-2 | 4999 | 0.050 | 0.057 | 0.061 | O6 | 0.04 |
| 32 | 15.66 | 610.3 | 3-Methyl-c-pentene-2 | 3606 | 0.036 | 0.041 | 0.044 | O6 | 0.09 |
| 33 | 15.82 | 612.5 | O13 | 194 | 0.002 | 0.002 | 0.002 | O6 | 0.19 |
| 34 | 15.93 | 614.1 | c-Hexene-2 | 1721 | 0.017 | 0.020 | 0.021 | O6 | 0.15 |
| 35 | 16.41 | 620.3 | 3,3-Dimethylpentene-1 | 5129 | 0.051 | 0.058 | 0.053 | O7 | 0.24 |
| 36 | 16.75 | 624.6 | 2,2-Dimethylpentane | 39185 | 0.403 | 0.473 | 0.409 | I7 | 0.09 |
| 37 | 16.96 | 627.1 | Methylcyclopentane | 33641 | 0.338 | 0.357 | 0.408 | N6 | 0.04 |
| 38 | 17.26 | 630.7 | 2,4-Dimethylpentane | 37925 | 0.389 | 0.458 | 0.394 | I7 | 0.29 |
| 39 | 17.74 | 636.2 | 2,2,3-Trimethylbutane | 6232 | 0.064 | 0.073 | 0.065 | I7 | 0.42 |
| 40 | 18.32 | 642.6 | O17 | 174 | 0.002 | 0.002 | 0.002 | O7 | 0.14 |
| 41 | 18.73 | 646.8 | 2,4-Dimethylpentene-1 | 807 | 0.008 | 0.009 | 0.008 | O7 | 0.22 |
| 42 | 19.07 | 650.3 | Benzene | 564898 | 5.266 | 4.745 | 6.852 | A6 | 0.27 |
| 43 | 19.29 | 652.5 | 3-Methylhexene-1 | 372 | 0.004 | 0.004 | 0.004 | O7 | 0.02 |

TABLE H-continued

P.I.A.N.O. ANALYSIS
by Analytical Automation Specialists, Inc.
Licensed to: Ashland Petroleum Co. - Catlettsburg, KY

| | | | | | | | | | |
|---|---|---|---|---|---|---|---|---|---|
| 44 | 19.61 | 655.6 | 3,3-Dimethylpentane | 38564 | 0.395 | 0.452 | 0.401 | I7 | 0.24 |
| 45 | 19.76 | 657.0 | 5-Methylhexene-1 | 322 | 0.003 | 0.004 | 0.003 | O7 | 0.22 |
| 46 | 19.93 | 658.7 | Cyclohexane | 1855 | 0.019 | 0.019 | 0.022 | N6 | 0.35 |
| 47 | 20.15 | 660.6 | 2-Methyl-t-hexene-3 | 1413 | 0.014 | 0.016 | 0.015 | O7 | 0.17 |
| 48 | 20.53 | 664.1 | 4-Methylhexene-1 | 570 | 0.006 | 0.006 | 0.006 | O7 | 0.23 |
| 49 | 20.78 | 687.3 | 4-Methyl-t/c-hexene-2 | 3328 | 0.033 | 0.038 | 0.035 | O7 | 0.09 |
| 50 | 20.97 | 667.9 | 2-Methylhexane | 249033 | 2.552 | 2.979 | 2.589 | I7 | 0.14 |
| 51 | 21.15 | 689.5 | 2,3-Dimethylpentane | 91381 | 0.937 | 1.067 | 0.950 | I7 | 0.01 |
| 52 | 21.47 | 672.2 | 1,1-Dimethylcyclopentane | 1935 | 0.019 | 0.020 | 0.020 | N7 | 0.01 |
| 53 | 21.98 | 676.4 | 3-Methylhexane | 307358 | 3.084 | 3.555 | 3.126 | I7 | 0.01 |
| 54 | 22.37 | 679.6 | 3,4-Dimethyl-c-pentene-2 | 1367 | 0.014 | 0.015 | 0.014 | O7 | 0.05 |
| 55 | 22.73 | 682.4 | 1c,3-Dimethylcyclopentane | 3599 | 0.036 | 0.038 | 0.037 | N7 | 0.15 |
| 56 | 23.09 | 685.0 | 1t,3-Dimethylcyclopentane | 3753 | 0.038 | 0.040 | 0.039 | N7 | 0.06 |
| 57 | 23.23 | 686.1 | 3-Ethylpentane | 32146 | 0.329 | 0.374 | 0.334 | I7 | 0.11 |
| 58 | 23.43 | 666.6 | 1t,2-Dimethylcyclopentane | 5758 | 0.058 | 0.061 | 0.060 | N7 | 0.18 |
| 59 | 23.66 | 669.3 | 2,2,4-Trimethylpentane | 2549 | 0.026 | 0.030 | 0.023 | I7 | 0.12 |
| 60 | 24.40 | 694.6 | 3-Methyl-c-hexene-3 | 1954 | 0.020 | 0.022 | 0.020 | O7 | 0.15 |
| 61 | 24.89 | 697.9 | t-Heptene-3 | 3190 | 0.032 | 0.036 | 0.033 | O7 | 0.29 |
| 62 | 25.20 | 700.0 | n-Heptane | 251194 | 2.575 | 2.962 | 2.611 | O7 | 0.00 |
| 63 | 25.46 | 702.0 | c-Heptene-3 | 8205 | 0.082 | 0.093 | 0.085 | O7 | 0.21 |
| 64 | 25.61 | 703.2 | 2-Methyl-2-hexene | 3164 | 0.032 | 0.035 | 0.033 | O7 | 0.08 |
| 65 | 25.87 | 705.2 | 3-Methyl-t-hexene-3 | 2497 | 0.025 | 0.029 | 0.026 | O7 | 0.45 |
| 66 | 26.11 | 706.9 | 3-Ethylpentene-2 | 1560 | 0.016 | 0.017 | 0.016 | O7 | 0.16 |
| 67 | 26.58 | 710.4 | c-Heptene-2 | 4265 | 0.043 | 0.048 | 0.044 | O7 | 0.23 |
| 68 | 27.21 | 714.9 | 2,3-Dimethylpentene-2 | 3700 | 0.037 | 0.040 | 0.038 | O7 | 0.48 |
| 69 | 28.07 | 720.8 | 1c,2-Dimethylcyclopentane | 1624 | 0.016 | 0.018 | 0.017 | N7 | 0.36 |
| 70 | 28.21 | 721.7 | Methylcyclohexane | 769 | 0.008 | 0.008 | 0.008 | N7 | 0.20 |
| 71 | 28.69 | 724.9 | 1,1,3-Trimethylcyclopentane | 18448 | 0.185 | 0.196 | 0.168 | N8 | 0.07 |
| 72 | 30.22 | 734.6 | Ethylcyclopentane | 1159 | 0.012 | 0.012 | 0.012 | N7 | 0.18 |
| 73 | 30.49 | 736.2 | 2,2,3-Trimethylpentane | 18360 | 0.188 | 0.208 | 0.167 | I8 | 0.04 |
| 74 | 30.83 | 738.3 | 2,4-Dimethylhexane | 31948 | 0.327 | 0.370 | 0.291 | I8 | 0.05 |
| 75 | 31.79 | 743.9 | 1c,2t,4-Trimethylcyclopentane | 2525 | 0.025 | 0.026 | 0.023 | N8 | 0.10 |
| 76 | 32.06 | 745.4 | 3,3-Dimethylhexane | 16012 | 0.164 | 0.183 | 0.146 | I8 | 0.22 |
| 77 | 32.90 | 750.1 | ? | 184 | 0.002 | 0.002 | 0.002 | | UNK |
| 78 | 33.12 | 751.3 | 1t,2c,3-Trimethylcyclopentane | 834 | 0.008 | 0.009 | 0.008 | N5 | 0.09 |
| 79 | 33.36 | 752.6 | O39 | 131 | 0.001 | 0.001 | 0.001 | O7 | 0.09 |
| 80 | 33.67 | 754.3 | 2,3,4-Trimethylpentane | 922 | 0.009 | 0.010 | 0.008 | I8 | 0.06 |
| 81 | 34.47 | 758.5 | Toluene | 1451924 | 13.616 | 12.438 | 15.020 | A7 | 0.16 |
| 82 | 34.72 | 759.8 | 2,3,3-Trimethylpentane | 1464 | 0.015 | 0.016 | 0.015 | I8 | 0.03 |
| 83 | 35.24 | 762.4 | O43 | 233 | 0.002 | 0.003 | 0.002 | O7 | 0.09 |
| 84 | 35.75 | 765.0 | 2,3-Dimethylhexane | 26195 | 0.268 | 0.298 | 0.238 | I8 | 0.37 |
| 85 | 35.97 | 766.1 | 2-Methyl-3-ethylpentane | 4415 | 0.045 | 0.050 | 0.040 | I8 | 0.46 |
| 86 | 36.17 | 767.0 | 1,1,2-Trimethylcyclopentane | 1431 | 0.014 | 0.015 | 0.013 | N8 | 0.20 |
| 87 | 36.97 | 770.9 | 2-Methylheptane | 83862 | 0.857 | 0.972 | 0.762 | I8 | 0.05 |
| 88 | 37.24 | 772.2 | 4-Methylheptane | 41947 | 0.429 | 0.482 | 0.381 | I8 | 0.25 |
| 89 | 37.41 | 773.0 | 3-Methyl-3-ethylpentane | 8542 | 0.087 | 0.097 | 0.078 | I8 | 0.06 |
| 90 | 37.51 | 773.4 | 3,4-Dimethylhexane | 6607 | 0.068 | 0.074 | 0.060 | I8 | 0.03 |
| 91 | 37.99 | 775.6 | 1,3c-Dimethylcyclohexane | 396 | 0.004 | 0.004 | 0.004 | N8 | 0.12 |
| 92 | 38.43 | 777.6 | 3-Methylheptane | 102921 | 1.052 | 1.180 | 0.936 | I8 | 0.22 |
| 93 | 38.61 | 778.5 | 1c,2t,3-Trimethylcyclopentane | 25484 | 0.256 | 0.263 | 0.232 | N8 | 0.47 |
| 94 | 40.58 | 787.1 | 2,2,5-Trimethylhexane | 2157 | 0.022 | 0.025 | 0.017 | I9 | 0.04 |
| 95 | 40.77 | 787.9 | 3c-Ethylmethylcyclopentane | 506 | 0.005 | 0.005 | 0.005 | N8 | 0.05 |
| 96 | 41.19 | 789.6 | 3t-Ethylmethylcyclopentane | 737 | 0.007 | 0.008 | 0.007 | N8 | 0.41 |
| 97 | 41.43 | 790.6 | 2t-Ethylmethylcyclopentane | 1124 | 0.011 | 0.012 | 0.010 | N8 | 0.33 |
| 98 | 41.62 | 791.4 | 1,1-Methylethylcyclopentane | 594 | 0.006 | 0.006 | 0.005 | N8 | 0.00 |
| 99 | 41.99 | 792.9 | 2,2,4-Trimethylhexane | 788 | 0.008 | 0.009 | 0.006 | I9 | 0.07 |
| 100 | 42.36 | 794.4 | 1t,2-Dimethylcyclohexane | 862 | 0.009 | 0.009 | 0.008 | N8 | 0.41 |
| 101 | 42.62 | 795.5 | t-Octene-4 | 933 | 0.009 | 0.010 | 0.008 | O8 | 0.06 |
| 102 | 43.19 | 797.7 | 1c,2c,3-Trimethylcyclopentane | 3050 | 0.031 | 0.031 | 0.028 | N8 | 0.07 |
| 103 | 43.49 | 798.9 | 1t,3 Dimethylcyclohexane | 291 | 0.003 | 0.003 | 0.003 | N8 | 0.01 |
| 104 | 43.77 | 800.0 | n-Octane | 95201 | 0.973 | 1.097 | 0.866 | P8 | 0.00 |
| 105 | 44.51 | 803.8 | 1c,4-Dimethylcyclohexane | 865 | 0.009 | 0.009 | 0.008 | N8 | 0.01 |
| 106 | 44.85 | 805.6 | Octene-2 | 616 | 0.006 | 0.007 | 0.006 | O8 | 0.01 |
| 107 | 45.17 | 807.2 | i-Propylcyclopentane | 1212 | 0.012 | 0.012 | 0.011 | N8 | 0.08 |
| 108 | 46.17 | 812.2 | ? | 414 | 0.004 | 0.004 | 0.004 | | UNK |
| 109 | 47.15 | 817.0 | 2,3,4-Trimethylhexane | 1200 | 0.012 | 0.013 | 0.010 | I9 | 0.50 |
| 110 | 47.97 | 820.9 | N3 | 4039 | 0.041 | 0.045 | 0.032 | N8 | 0.47 |
| 111 | 48.91 | 825.3 | 2,3,4 Trimethylhexane | 4448 | 0.045 | 0.046 | 0.041 | I9 | 0.39 |
| 112 | 49.29 | 827.0 | 2,2-Dimethylheptane | 698 | 0.007 | 0.007 | 0.006 | I9 | 0.61 |
| 113 | 50.23 | 831.3 | N4 | 1200 | 0.012 | 0.013 | 0.010 | N8 | 0.49 |
| 114 | 50.47 | 832.3 | 2,2,3-Trimethylhexane | 2769 | 0.028 | 0.032 | 0.022 | I9 | 0.33 |
| 115 | 52.05 | 839.3 | n-Propylcyclopentane | 9004 | 0.090 | 0.092 | 0.082 | N8 | 0.26 |
| 116 | 52.39 | 840.7 | 2,6-Dimethylheptane | 4228 | 0.043 | 0.047 | 0.034 | I9 | 0.48 |
| 117 | 54.49 | 849.4 | Ethylbenzene | 341264 | 3.242 | 2.962 | 3.104 | A8 | 0.34 |
| 118 | 54.95 | 851.3 | 1c,2t,4t-Trimethylcyclohexane | 754 | 0.008 | 0.008 | 0.006 | N9 | 0.59 |

TABLE H-continued

P.I.A.N.O. ANALYSIS
by Analytical Automation Specialists, Inc.
Licensed to: Ashland Petroleum Co. - Catlettsburg, KY

| | | | | | | | | | |
|---|---|---|---|---|---|---|---|---|---|
| 119 | 56.99 | 859.4 | m-Xylene | 726750 | 6.905 | 6.328 | 6.610 | A8 | 0.10 |
| 120 | 57.25 | 860.4 | p-Xylene | 303352 | 2.882 | 2.651 | 2.759 | A8 | 0.20 |
| 121 | 57.56 | 861.6 | 2,3-Dimethylheptane | 5225 | 0.053 | 0.058 | 0.042 | I9 | 0.12 |
| 122 | 58.07 | 863.5 | 3,4-Dimethylheptane | 1431 | 0.015 | 0.016 | 0.012 | I9 | 0.13 |
| 123 | 58.31 | 864.4 | 3,4-Dimethylheptane | 2495 | 0.025 | 0.028 | 0.020 | I9 | 0.11 |
| 124 | 59.01 | 867.1 | I4 | 3424 | 0.035 | 0.038 | 0.028 | I9 | 0.14 |
| 125 | 59.93 | 870.4 | 4-Methyloctane | 16036 | 0.164 | 0.180 | 0.130 | I9 | 0.43 |
| 126 | 60.24 | 871.6 | 2-Methyloctane | 17708 | 0.181 | 0.200 | 0.143 | I9 | 0.07 |
| 127 | 61.67 | 876.7 | 3-Ethylheptane | 5188 | 0.053 | 0.058 | 0.042 | I9 | 0.01 |
| 128 | 62.09 | 878.2 | 3-Methyloctane | 20667 | 0.211 | 0.232 | 0.167 | I9 | 0.57 |
| 129 | 63.04 | 881.5 | o-Xylene | 511912 | 4.864 | 4.376 | 4.656 | A8 | 0.01 |
| 130 | 68.66 | 900.0 | n-Nonane | 24833 | 0.253 | 0.279 | 0.201 | P9 | 0.00 |
| 131 | 70.45 | 911.9 | i-Propylbenzene | 45800 | 0.438 | 0.402 | 0.370 | A9 | 0.20 |
| 132 | 72.45 | 924.8 | 2,4-Dimethyloctane | 1350 | 0.014 | 0.015 | 0.010 | I10 | 0.31 |
| 133 | 73.83 | 933.4 | 2,5-Dimethyloctane | 520 | 0.005 | 0.006 | 0.004 | I10 | 0.22 |
| 134 | 75.41 | 943.2 | 3,3-Dimethyloctane | 589 | 0.006 | 0.006 | 0.004 | I10 | 0.57 |
| 135 | 75.97 | 946.5 | n-Propylbenzene | 135770 | 1.298 | 1.193 | 1.098 | A9 | 0.11 |
| 136 | 77.35 | 954.8 | 1-Methyl-3-ethylbenzene | 313218 | 2.995 | 2.744 | 2.533 | A9 | 0.09 |
| 137 | 77.65 | 956.5 | 1-Methyl-4-ethylbenzene | 146039 | 1.397 | 1.284 | 1.181 | A9 | 0.31 |
| 138 | 78.61 | 962.1 | 1,3,5-Trimethylbenzene | 119399 | 1.142 | 1.045 | 0.966 | A9 | 0.08 |
| 139 | 79.00 | 964.4 | I15 | 812 | 0.008 | 0.009 | 0.006 | I10 | 0.50 |
| 140 | 79.70 | 968.4 | 5-Methylnonane | 1011 | 0.010 | 0.011 | 0.007 | I10 | 0.32 |
| 141 | 80.06 | 970.5 | 1-Methyl-2-ethylbenzene | 172351 | 1.648 | 1.482 | 1.394 | A9 | 0.17 |
| 142 | 80.38 | 972.3 | 2-Methylnonane | 2960 | 0.030 | 0.033 | 0.022 | I10 | 0.29 |
| 143 | 80.86 | 975.0 | N35 | 572 | 0.006 | 0.006 | 0.004 | N10 | 0.00 |
| 144 | 81.40 | 978.0 | N29 | 3280 | 0.033 | 0.033 | 0.024 | N10 | 0.18 |
| 145 | 82.01 | 981.4 | ? | 582 | 0.006 | 0.006 | 0.004 | | UNK |
| 146 | 82.46 | 983.9 | 1,2,4-Trimethylbenzene | 592716 | 5.704 | 5.158 | 4.824 | A9 | 0.10 |
| 147 | 84.61 | 995.6 | i-Butylbenzene | 15732 | 0.151 | 0.140 | 0.115 | A10 | 0.04 |
| 148 | 84.98 | 997.6 | sec-Butylbenzene | 16591 | 0.160 | 0.147 | 0.121 | A10 | 0.35 |
| 149 | 85.44 | 1000.0 | n-Decane | 4291 | 0.044 | 0.047 | 0.031 | P10 | 0.00 |
| 150 | 86.18 | 1006.7 | 1,2,3-Trimethylbenzene | 182538 | 1.746 | 1.546 | 1.476 | A9 | 0.01 |
| 151 | 86.47 | 1009.3 | 1-Methyl-3-i-propylbenzene | 28786 | 0.277 | 0.255 | 0.210 | A10 | 0.27 |
| 152 | 86.87 | 1012.9 | 1-Methyl-4-i-propylbenzene | 8697 | 0.084 | 0.077 | 0.063 | A10 | 0.10 |
| 153 | 87.57 | 1019.1 | 2,3-Dihydroindene | 38559 | 0.369 | 0.303 | 0.317 | A9 | 0.03 |
| 154 | 88.34 | 1025.9 | ? | 2880 | 0.030 | 0.024 | 0.025 | | UNK |
| 155 | 88.53 | 1027.6 | 1-Methyl-2-i-propylbenzene | 1835 | 0.018 | 0.016 | 0.013 | A10 | 0.33 |
| 156 | 89.91 | 1039.5 | 1,3-Diethylbenzene | 32931 | 0.317 | 0.290 | 0.240 | A10 | 0.04 |
| 157 | 90.25 | 1042.4 | 1-Methyl-3-n-propylbenzene | 91183 | 0.877 | 0.806 | 0.664 | A10 | 0.10 |
| 158 | 90.70 | 1046.3 | 1-Methyl-4-n-propylbenzene | 53844 | 0.518 | 0.478 | 0.392 | A10 | 0.53 |
| 159 | 90.81 | 1047.2 | n-Butylbenzene | 29713 | 0.286 | 0.263 | 0.216 | A10 | 0.67 |
| 160 | 91.08 | 1049.5 | 1,3-Dimethyl-5-ethylbenzene | 68764 | 0.661 | 0.595 | 0.501 | A10 | 0.30 |
| 161 | 91.31 | 1051.5 | 1,2-Diethylbenzene | 8226 | 0.079 | 0.071 | 0.060 | A10 | 0.08 |
| 162 | 92.06 | 1057.8 | 1-Methyl-2-n-propylbenzene | 49398 | 0.475 | 0.431 | 0.360 | A10 | 0.56 |
| 163 | 93.27 | 1067.9 | 1,4,Dimethyl-2-ethylbenzene | 67411 | 0.648 | 0.585 | 0.491 | A10 | 0.06 |
| 164 | 93.47 | 1069.5 | s-C5Bz/1,3-DM-4-EtBz | 62923 | 0.607 | 0.559 | 0.416 | A11 | 0.11 |
| 165 | 93.73 | 1071.6 | ? | 402 | 0.004 | 0.004 | 0.003 | | UNK |
| 166 | 94.16 | 1075.2 | 1,2-Dimethyl-4-ethylbenzene | 117136 | 1.126 | 1.020 | 0.853 | A10 | 0.15 |
| 167 | 94.81 | 1080.4 | 1,3-Dimethyl-2-ethylbenzene | 10121 | 0.097 | 0.087 | 0.074 | A10 | 0.02 |
| 168 | 96.19 | 1091.5 | 1-Methyl-4-t-butylbenzene | 6213 | 0.060 | 0.056 | 0.041 | A11 | 0.34 |
| 169 | 96.34 | 1092.8 | 1,2-Dimethyl-3-ethylbenzene | 40170 | 0.386 | 0.343 | 0.292 | A10 | 0.27 |
| 170 | 96.87 | 1097.0 | ? | 1540 | 0.016 | 0.014 | 0.012 | | UNK |
| 171 | 97.08 | 1098.7 | ? | 1454 | 0.015 | 0.013 | 0.011 | | UNK |
| 172 | 97.53 | 1103.2 | ? | 2161 | 0.022 | 0.020 | 0.017 | | UNK |
| 173 | 97.68 | 1104.8 | 1,2,4,5-Tetramethylbenzene | 67999 | 0.654 | 0.583 | 0.495 | A10 | 0.00 |
| 174 | 98.05 | 1108.9 | 1,2,3,5-Tetramethylbenzene | 105027 | 1.010 | 0.898 | 0.765 | A10 | 0.02 |
| 175 | 98.35 | 1112.3 | ? | 338 | 0.003 | 0.003 | 0.003 | | UNK |
| 176 | 98.68 | 1115.9 | ? | 1124 | 0.012 | 0.010 | 0.009 | | UNK |
| 177 | 98.93 | 1118.7 | ? | 319 | 0.003 | 0.003 | 0.002 | | UNK |
| 178 | 99.19 | 1121.5 | 1-t-Butyl-2-methylbenzene | 176 | 0.002 | 0.002 | 0.001 | A11 | 0.73 |
| 179 | 99.76 | 1127.7 | 5-Methylindan | 25105 | 0.242 | 0.215 | 0.166 | A11 | 0.13 |
| 180 | 100.29 | 1133.5 | A3 | 8118 | 0.078 | 0.070 | 0.054 | A11 | 0.12 |
| 181 | 100.42 | 1134.9 | ? | 1746 | 0.018 | 0.016 | 0.012 | | UNK |
| 182 | 100.58 | 1136.6 | ? | 13557 | 0.139 | 0.124 | 0.095 | | UNK |
| 183 | 100.77 | 1138.7 | 1-Ethyl-2-n-propylbenzene | 24129 | 0.233 | 0.207 | 0.160 | A11 | 0.09 |
| 184 | 100.99 | 1141.1 | 1-Methyl-3-n-butylbenzene | 1199 | 0.012 | 0.010 | 0.008 | A11 | 0.38 |
| 185 | 101.23 | 1143.6 | s-Pentylbenzene | 35349 | 0.341 | 0.303 | 0.234 | A11 | 0.09 |
| 186 | 101.72 | 1148.9 | n-Pentylbenzene | 2802 | 0.027 | 0.024 | 0.019 | A11 | 0.53 |
| 187 | 101.89 | 1150.6 | 1t-M-2-(4-MP)cyclopentane | 3618 | 0.036 | 0.036 | 0.022 | N12 | 0.16 |
| 188 | 102.19 | 1153.9 | ? | 16966 | 0.174 | 0.172 | 0.107 | | UNK |
| 189 | 102.62 | 1158.4 | 1,4-Di-i-propylbenzene | 8582 | 0.083 | 0.074 | 0.052 | A12 | 0.77 |
| 190 | 102.79 | 1160.2 | ? | 10567 | 0.108 | 0.096 | 0.068 | | UNK |
| 191 | 103.18 | 1164.3 | ? | 518 | 0.005 | 0.005 | 0.003 | | UNK |
| 192 | 103.46 | 1167.3 | ? | 17599 | 0.180 | 0.161 | 0.113 | | UNK |
| 193 | 103.65 | 1169.2 | Naphthalene | 46942 | 0.451 | 0.349 | 0.358 | A10 | 0.12 |

TABLE H-continued

P.I.A.N.O. ANALYSIS
by Analytical Automation Specialists, Inc.
Licensed to: Ashland Petroleum Co. - Catlettsburg, KY

| | | | | | | | | | |
|---|---|---|---|---|---|---|---|---|---|
| 194 | 104.21 | 1175.1 | ? | 641 | 0.007 | 0.005 | 0.005 | | UNK |
| 195 | 104.65 | 1179.7 | I46 | 5710 | 0.058 | 0.061 | 0.035 | I12 | 0.30 |
| 196 | 104.77 | 1180.9 | ? | 952 | 0.010 | 0.010 | 0.006 | | UNK |
| 197 | 105.14 | 1184.7 | ? | 6019 | 0.062 | 0.065 | 0.037 | | UNK |
| 198 | 105.53 | 1188.7 | 1,3-Di-n-propylbenzene | 1105 | 0.011 | 0.010 | 0.007 | A12 | 0.20 |
| 199 | 105.66 | 1190.1 | A5 | 21053 | 0.204 | 0.181 | 0.128 | A12 | 0.47 |
| 200 | 105.81 | 1191.6 | ? | 13470 | 0.138 | 0.123 | 0.086 | | UNK |
| 201 | 106.63 | 1200.0 | n-Dodecane | 14222 | 0.145 | 0.152 | 0.086 | P12 | 0.00 |
| 202 | 107.47 | 1210.0 | ? | 1990 | 0.020 | 0.021 | 0.012 | | UNK |
| 203 | 108.07 | 1217.1 | ? | 701 | 0.007 | 0.008 | 0.004 | | UNK |
| 204 | 108.17 | 1218.3 | ? | 1208 | 0.012 | 0.013 | 0.007 | | UNK |
| 205 | 108.63 | 1223.7 | ? | 1480 | 0.015 | 0.016 | 0.009 | | UNK |
| 206 | 108.88 | 1226.6 | 1,2,4-Triethylbenzene | 5638 | 0.055 | 0.049 | 0.034 | A12 | 0.16 |
| 207 | 109.09 | 1229.1 | ? | 217 | 0.002 | 0.002 | 0.001 | | UNK |
| 208 | 109.71 | 1236.3 | ? | 270 | 0.003 | 0.002 | 0.002 | | UNK |
| 209 | 109.81 | 1237.5 | ? | 465 | 0.005 | 0.004 | 0.003 | | UNK |
| 210 | 110.22 | 1242.3 | 1-Methyl-4-n-pentylbenzene | 6208 | 0.060 | 0.054 | 0.038 | A12 | 0.25 |
| 211 | 110.56 | 1246.2 | ? | 601 | 0.006 | 0.005 | 0.004 | | UNK |
| 212 | 110.75 | 1248.4 | ? | 410 | 0.004 | 0.004 | 0.003 | | UNK |
| 213 | 111.39 | 1255.7 | ? | 3178 | 0.033 | 0.029 | 0.020 | | UNK |
| 214 | 111.71 | 1259.4 | ? | 1762 | 0.018 | 0.016 | 0.011 | | UNK |
| 215 | 112.10 | 1263.8 | ? | 439 | 0.005 | 0.004 | 0.003 | | UNK |
| 216 | 112.96 | 1273.6 | A1274 | 22408 | 0.217 | 0.227 | 0.120 | A12 | 0.64 |
| 217 | 113.67 | 1281.6 | 2-Methylnaphthalene | 41140 | 0.397 | 0.308 | 0.282 | A11 | 0.68 |
| 218 | 114.05 | 1285.8 | ? | 861 | 0.009 | 0.007 | 0.006 | | UNK |
| 219 | 114.98 | 1296.1 | 1-Methylnaphthalene | 27764 | 0.268 | 0.208 | 0.190 | A11 | 0.03 |
| 220 | 116.12 | 1400.0 | C14+ | 351 | 0.004 | 0.004 | 0.002 | + | 0.00 |
| 221 | 117.55 | 1400.0 | C14+ | 307 | 0.003 | 0.003 | 0.002 | + | 0.00 |
| 222 | 119.04 | 1400.0 | C14+ | 466 | 0.005 | 0.005 | 0.002 | + | 0.00 |
| 223 | 119.98 | 1400.0 | C14+ | 361 | 0.004 | 0.004 | 0.002 | + | 0.00 |
| 224 | 121.51 | 1400.0 | C14+ | 2623 | 0.027 | 0.028 | 0.014 | + | 0.00 |
| 225 | 121.65 | 1400.0 | C14+ | 798 | 0.008 | 0.008 | 0.004 | + | 0.00 |
| 226 | 121.77 | 1400.0 | C14+ | 1464 | 0.015 | 0.015 | 0.008 | + | 0.00 |
| 227 | 122.37 | 1400.0 | C14+ | 3591 | 0.036 | 0.038 | 0.019 | + | 0.00 |
| 228 | 122.51 | 1400.0 | C14+ | 2865 | 0.029 | 0.030 | 0.015 | + | 0.00 |
| 229 | 123.46 | 1400.0 | C14+ | 9089 | 0.092 | 0.096 | 0.047 | + | 0.00 |
| 230 | 123.73 | 1400.0 | C14+ | 4177 | 0.042 | 0.044 | 0.022 | + | 0.00 |
| 231 | 124.93 | 1400.0 | C14+ | 3559 | 0.036 | 0.037 | 0.019 | + | 0.00 |
| 232 | 125.10 | 1400.0 | C14+ | 1019 | 0.010 | 0.011 | 0.005 | + | 0.00 |
| 233 | 125.99 | 1400.0 | C14+ | 3682 | 0.037 | 0.039 | 0.019 | + | 0.00 |
| 234 | 127.69 | 1400.0 | C14+ | 397 | 0.004 | 0.004 | 0.002 | + | 0.00 |
| 235 | 128.38 | 1400.0 | C14+ | 598 | 0.006 | 0.006 | 0.003 | + | 0.00 |
| 236 | 129.12 | 1400.0 | C14+ | 290 | 0.003 | 0.003 | 0.002 | + | 0.00 |
| 237 | 129.55 | 1400.0 | C14+ | 1338 | 0.014 | 0.014 | 0.007 | + | 0.00 |
| 238 | 129.88 | 1400.0 | C14+ | 261 | 0.003 | 0.003 | 0.001 | + | 0.00 |
| 239 | 130.21 | 1400.0 | C14+ | 659 | 0.007 | 0.007 | 0.003 | + | 0.00 |
| 240 | 130.73 | 1400.0 | C14+ | 513 | 0.005 | 0.005 | 0.003 | + | 0.00 |
| 241 | 131.05 | 1400.0 | C14+ | 1161 | 0.012 | 0.012 | 0.006 | + | 0.00 |
| 242 | 131.44 | 1400.0 | C14+ | 1109 | 0.011 | 0.012 | 0.006 | + | 0.00 |
| 243 | 132.47 | 1400.0 | C14+ | 1028 | 0.010 | 0.011 | 0.005 | + | 0.00 |
| 244 | 132.77 | 1400.0 | C14+ | 1015 | 0.010 | 0.011 | 0.005 | + | 0.00 |
| 245 | 133.51 | 1400.0 | C14+ | 706 | 0.007 | 0.007 | 0.004 | + | 0.00 |
| 246 | 133.66 | 1400.0 | C14+ | 508 | 0.005 | 0.005 | 0.003 | + | 0.00 |
| 247 | 133.77 | 1400.0 | C14+ | 1123 | 0.011 | 0.012 | 0.006 | + | 0.00 |
| 248 | 134.71 | 1400.0 | C14+ | 1493 | 0.015 | 0.016 | 0.008 | + | 0.00 |
| 249 | 135.21 | 1400.0 | C14+ | 379 | 0.004 | 0.004 | 0.002 | + | 0.00 |
| 250 | 135.51 | 1400.0 | C14+ | 279 | 0.003 | 0.003 | 0.001 | + | 0.00 |
| 251 | 136.37 | 1400.0 | C14+ | 409 | 0.004 | 0.004 | 0.002 | + | 0.00 |
| 252 | 140.65 | 1400.0 | C14+ | 269 | 0.003 | 0.003 | 0.001 | + | 0.00 |
| 253 | 141.68 | 1400.0 | C14+ | 601 | 0.006 | 0.006 | 0.003 | + | 0.00 |

What is claimed is:

1. In a process for the analysis of a mixture of liquid hydrocarbons comprising a chemical species to determine species concentration, the improvement comprising in combination:

a) measuring the near infrared absorption in at least two of the bands of:

1) For benzene: 850–925 nm and/or 1120–1260 nm and/or 1600–1670 nm and/or 1780–1858 nm and/or 2100–2160 nanometers (nm);

2) For toluene: 860–910 nm and/or 975–1000 nm and/or 1214–1230 nm and/or 1600–1670 nm and/or 1780–1858 nm and/or 2000–2160 nm;

3) For xylenes: 850–930 nm and/or 940–990 nm and/or 1015–1045 nm and/or 1120–1214 nm and/or 1320–1530 nm and/or 1600–1670 nm and/or 1780–1858 nm and/or 2000–2040 nm and/or 2100–2160 nm;

4) For alkyl benzenes: 850–900 nm and/or 1015–1045 nm and/or 1156–1264 nm and/or 1214–1230 nm and/or 1214–1264 nm, and/or 1320–1480 nm and/or 1600–1670 nm and/or 1970–2040 nm;

5) For n-paraffins: 1156–1264 nm and/or 1320–1480 nm and/or 1600–1670 nm and/or 1780–1858 nm and/or 1940–2100 nm;

6) For isoparaffins: 1156–1264 nm and/or 1320–1500 nm and/or 1560–1670 nm and/or 1780–1858 nm, and/or 1900–2160 nm;

7) For naphthenes: 1156–1430 nm and/or 1780–1858 nm; or

8) For olefins: 1132–1214 nm; and/or 1600–1670 nm;

b) taking each of the absorbances measured, or a mathematical function thereof;

c) performing multiple regression analysis, partial least squares analysis, or other statistical treatment using the above absorbances or functions as individual independent variables, d) assigning and applying weighting constants or their equivalents to said independent variables, e) applying the above steps using known compositions to calibrate the instrument and determine said weighting constants or equivalents, f) outputting a signal indicative of the species concentration in the mixture, based on said absorbances or functions.

2. A process according to claim 1 wherein said mixture comprises ethyl-benzene and wherein at least two bands are used and said bands are 1156–1214 nm, 1600–1670 nm, and 1214–1230 nm or 1230–1264.

3. A process according to claim 1 wherein said mixture comprises benzene and wherein at least two bands are used and said bands are 2100–2160 nm, 1600–1670 nm, and 1780–1858 nm.

4. A process according to claim 1 wherein said mixture comprises toluene and wherein at least two bands are used and said bands are 1670 nm, 1780–1858 nm, and 1214–1230 nm.

5. A process according to claim 1 wherein said statistical treatment comprises partial least squares analysis over the length of each band, of wavelengths, or of a portion thereof.

6. A process according to claim 1 wherein said mixture flows substantially intermittently or continuously past the point of measuring said absorbance.

7. A process according to claim 1 wherein a derivative of said absorbance is computed.

8. A process according to claim 1 wherein said mathematical converting comprises a baseline off-set correction.

9. A process according to claim 1 wherein said mathematically converting comprises partial least squares analyses, principle component regression, Gauss-Jordan Row reduction, or multiple linear regression.

10. A process according to claim 1 wherein the hydrocarbon is a refinery blending stream and said absorbance is also indicative of benzene content.

11. A process according to claim 1 wherein said signal controls a fuel blending system feeding blending components having different benzene compositions into a common zone, whereby a product having a desired benzene composition is produced.

12. A process according to claim 1 wherein the hydrocarbons being monitored are involved in a chemical reaction.

13. A process according to claim 1 said hydrocarbons comprise reformate from a reforming step, and wherein said signal is used to control the severity of said reforming step by adjusting throughput, hydrogen uptake, temperature, or unit space velocity.

14. A process according to claim 1 said hydrocarbons comprise product from a catalytic cracking step, and wherein said signal is used to control the severity of said catalytic cracking step by adjusting catalyst:oil ratio, temperature, or recycle of naphtha or other cracked product.

15. A process according to claim 1 said hydrocarbons comprise product from an alkylation step, and wherein said signal is used to control isoparaffin:olefin ratio.

16. A process according to claim 1 said hydrocarbons comprise product from an ether manufacturing step, and wherein said signal is used to control alcohol:isoolefin ratio.

17. A process according to claim 1 said hydrocarbons comprise product from an isomerization step, and wherein said signal is used to control isoparaffin:normal paraffin ratio.

18. A process according to claim 1 wherein a second derivative of absorbances are measured.

* * * * *